United States Patent
Hirokawa et al.

(10) Patent No.: US 7,813,471 B2
(45) Date of Patent: Oct. 12, 2010

(54) X-RAY CT APPARATUS

(75) Inventors: Koichi Hirokawa, Tokyo (JP); Taiga Goto, Tokyo (JP); Yoshiaki Sugaya, Tokyo (JP); Osamu Miyazaki, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 167 days.

(21) Appl. No.: 12/301,713

(22) PCT Filed: May 24, 2007

(86) PCT No.: PCT/JP2007/060621

§ 371 (c)(1),
(2), (4) Date: Nov. 20, 2008

(87) PCT Pub. No.: WO2007/138979

PCT Pub. Date: Dec. 6, 2007

(65) Prior Publication Data

US 2009/0141854 A1   Jun. 4, 2009

(30) Foreign Application Priority Data

| May 25, 2006 | (JP) | ............................. 2006-144901 |
| Oct. 11, 2006 | (JP) | ............................. 2006-277699 |

(51) Int. Cl.
 *A61B 6/00* (2006.01)
(52) U.S. Cl. ........................................................ 378/4
(58) Field of Classification Search ...................... 378/4
 See application file for complete search history.

(56) References Cited

U.S. PATENT DOCUMENTS

| 2002/0075997 | A1* | 6/2002 | Unger et al. ............... 378/98.9 |
| 2003/0016778 | A1* | 1/2003 | Tachizaki et al. .............. 378/4 |
| 2004/0086076 | A1* | 5/2004 | Nagaoka et al. ................ 378/4 |
| 2005/0008115 | A1* | 1/2005 | Tsukagoshi .................... 378/4 |
| 2006/0018425 | A1* | 1/2006 | Nabatame .................... 378/16 |

FOREIGN PATENT DOCUMENTS

| JP | 11-299765 | 11/1999 |
| JP | 2006-116137 | 5/2006 |

* cited by examiner

*Primary Examiner*—Edward J Glick
*Assistant Examiner*—Alexander H Taningco
(74) *Attorney, Agent, or Firm*—Cooper & Dunham LLP

(57) ABSTRACT

An X-ray CT apparatus is provided, having a function for deciding an X-ray imaging condition prior to scanning, the X-ray imaging condition allowing an acquisition of contrast to noise ratio appropriate for identifying a diagnostic object. Prior to the real scan, a three-dimensional model of an object is estimated from scanogram projection data of the object, a contrast to noise ratio enabling identification of the diagnostic object is calculated, based on the diagnostic object size set by an operator via an operating device when planning the scan, the three-dimensional model, and a standard imaging condition that is stored in a storage device. Then, an optimum irradiated X-ray condition (tube current and tube voltage) is calculated for achieving the contrast to noise ratio enabling identification. The X-ray condition being calculated is displayed in the form of information such as image SD value and exposure dose, under the calculated X-ray condition and under other condition.

20 Claims, 18 Drawing Sheets

FIG.8
(a) 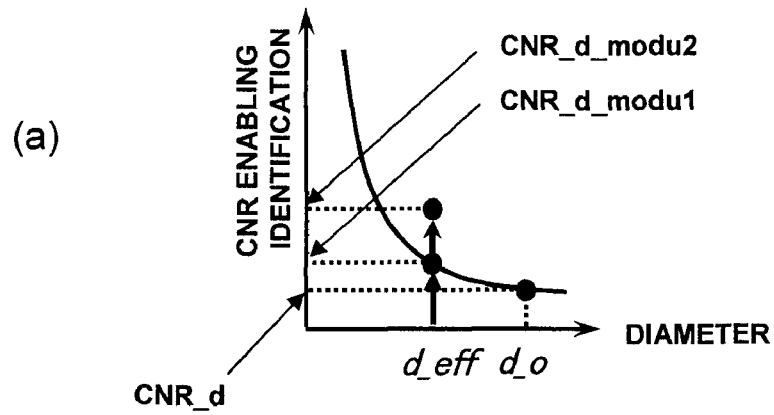
(b) 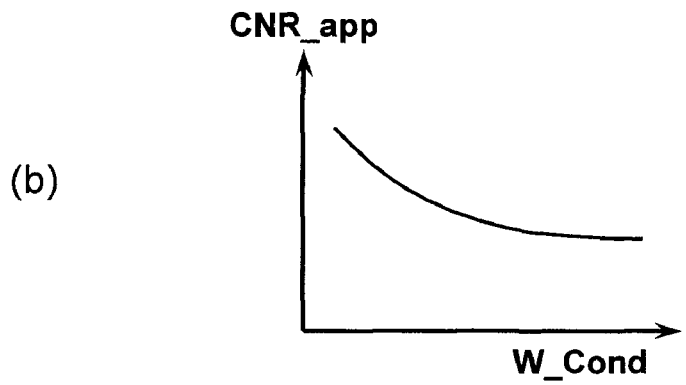
FIG.9
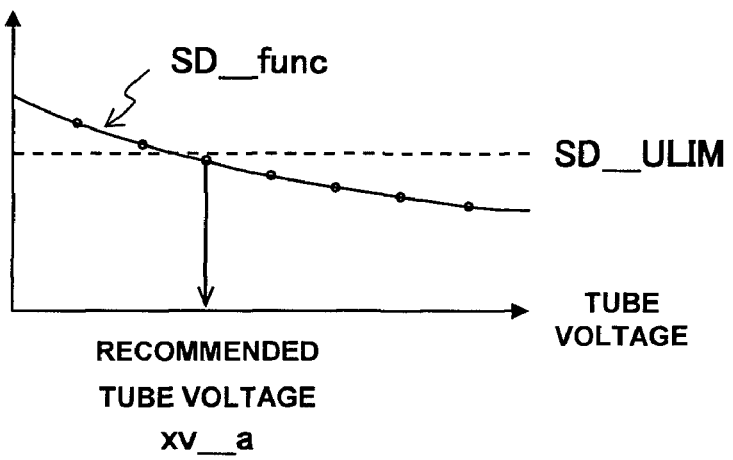

FIG.10

| RECOMMENDED CONDITION | OPTIMIZE TUBE CURRENT ONLY | NO OPTIMIZATION |
|---|---|---|
| TUBE VOLTAGE [kV]<br>*<br>AVERAGE TUBE CURRENT [mA]<br>*.*<br>CTDI [mGy]<br>**.*<br>IMAGE SD PREDICTIVE VALUE<br>.<br>IDENTIFIABLE SIZE[mm]<br>**.* | TUBE VOLTAGE [kV]<br>*<br>AVERAGE TUBE CURRENT [mA]<br>*.*<br>CTDI [mGy]<br>**.*<br>IMAGE SD PREDICTIVE VALUE<br>.<br>IDENTIFIABLE SIZE[mm]<br>**.* | TUBE VOLTAGE [kV]<br>*<br>AVERAGE TUBE CURRENT [mA]<br>*.*<br>CTDI [mGy]<br>**.*<br>IMAGE SD PREDICTIVE VALUE<br>. ~ .<br>IDENTIFIABLE SIZE[mm]<br>**.* ~ **.* |

TUBE VOLTAGE = STANDARD TUBE VOLTAGE xv_ref, HU_init

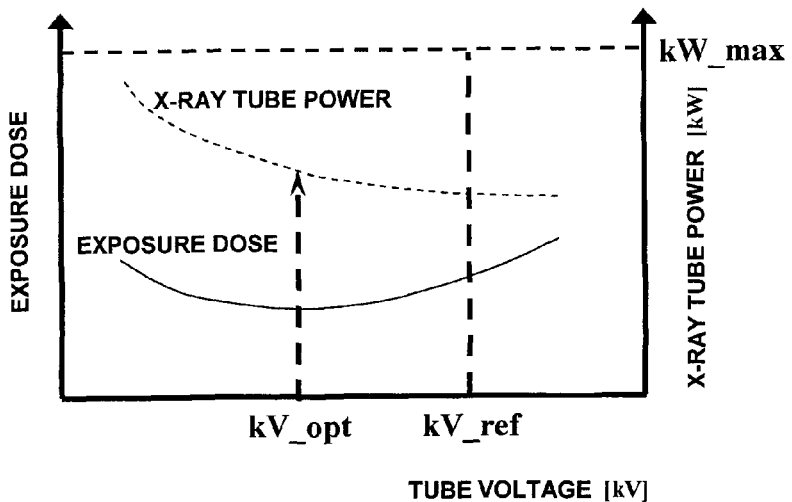

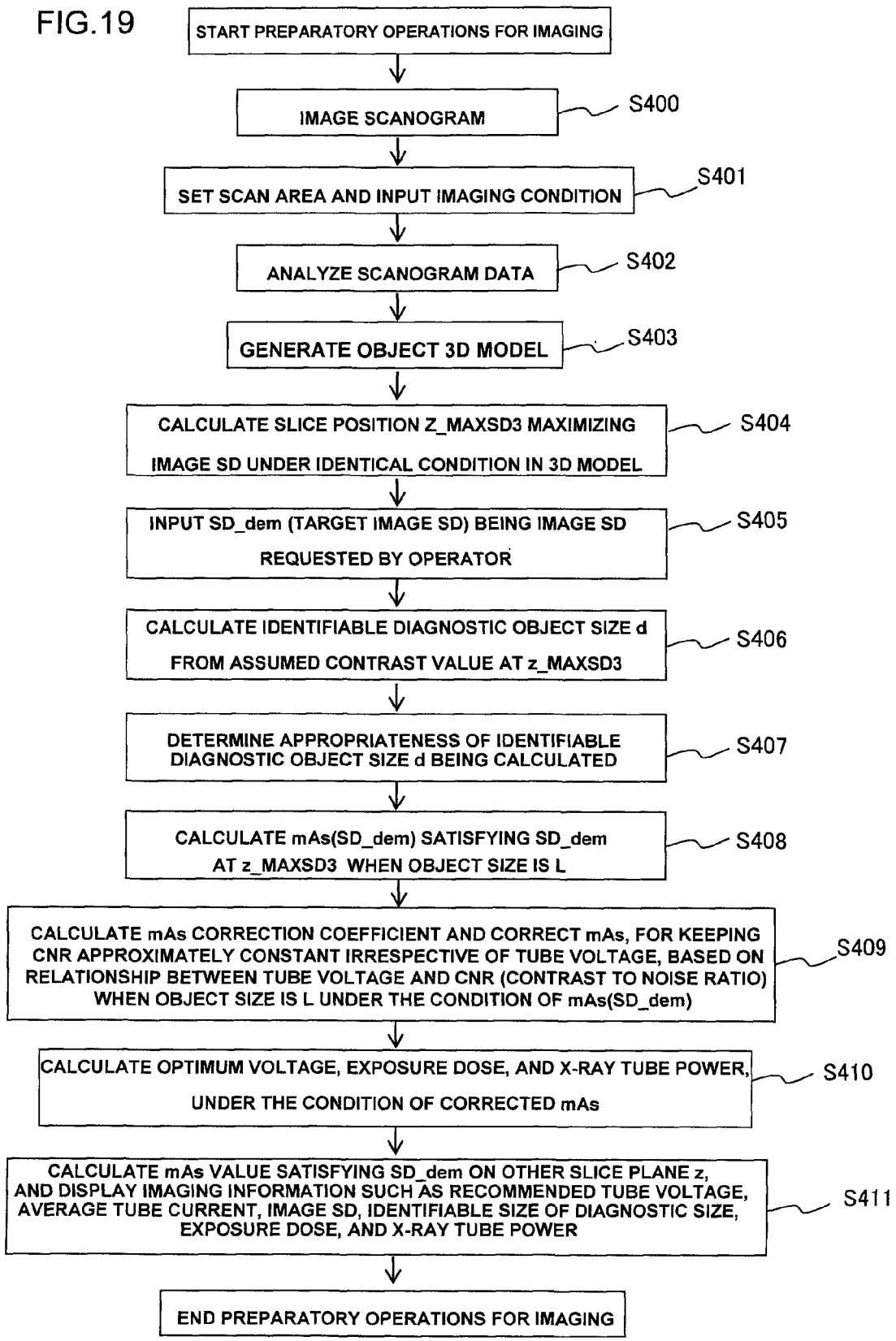

POSITION WHERE DIAMETER r DETERMINATION IS UNAVAILABLE

APPLY DEVICE MARGINAL OUTPUT : ●

SLICE POSITION WHERE
CNR_d IS NOT ATTAINABLE

X-RAY CT APPARATUS

TECHNICAL FIELD

The present invention relates to an X-ray CT apparatus, and more particularly, it relates to an X-ray CT apparatus having a function which decides in advance an X-ray condition before starting a scan, so as to obtain a contrast to noise ratio appropriate for identifying a diagnostic object.

BACKGROUND ART

There are two types of the X-ray CT apparatus; a single-slice X-ray CT apparatus for obtaining one tomographic image by one-time X-ray exposure, and a multi-slice X-ray CT apparatus being able to obtain multiple tomographic images simultaneously.

The single-slice X-ray CT apparatus employs an X-ray detector in which numerous X-ray detector elements are arranged in one line, i.e., in one-dimensional direction (channel direction), so as to irradiate a fan beam, i.e., a fan-shaped X-ray beam on an object from an X-ray tube, and measure the X-ray that has passed through the object to obtain projection data of the object.

On the other hand, the multi-slice X-ray CT apparatus irradiates a corn beam, i.e., a conical or a pyramidal X-ray beam from an X-ray tube, and an X-ray detector in which numerous X-ray detector elements are arranged in two-dimensional directions (the channel direction and row direction) measures the X-ray that has passed through the object to obtain projection data of the object.

In either type of the X-ray CT apparatus, the X-ray tube and the X-ray detector opposed to each other are rotated around the object, so as to collect projection data from multiple directions. The projection data being collected is subjected to a reconstruction filtering process for deblurring, and it is further subjected to back projection to reconstruct a tomographic image of the object.

The projection data is collected at discrete locations (hereinafter, each referred to as a "view") of the X-ray tube, and this collected projection data is referred to as "projection data at the view". The number of views per rotation of the X-ray tube and the X-ray detector for going around the object generally extends from several hundred to several thousand. An action for collecting the projection data of the number of views necessary for reconstructing one piece of CT image is referred to as "scan". The projection data corresponding to one view is made up of data in association with the number of channels times the number of rows of the X-ray detector described above (in the case of the single-slice X-ray CT apparatus, the number of row is equal to 1 as described above).

In the X-ray CT apparatus as discussed above, in order to identify a diagnostic object within the tomographic image being obtained, a contrast to noise ratio (Contrast to Noise Ratio, hereinafter, described as "CNR") serves as a significant image quality index. The CNR is a value obtained by dividing an absolute value of CT value difference between the diagnostic object and its surroundings, by an image noise standard deviation value (hereinafter, described as "image SD (Standard Deviation) value".

As for the aforementioned image quality index of the X-ray CT apparatus, increasing of exposure dose generally improves the CNR, and produces a good-quality image as an image for diagnosis. On the other hand, it is desirable to reduce to a minimum the exposure dose to a patient. Considering the situation above, the patent document 1 discloses an X-ray CT apparatus which improves the CNR in the reconstructed image by using a tube voltage (a voltage applied between anode and cathode of the X-ray tube) lower than conventionally used voltage, while not increasing the exposure dose and the image SD value, or which reduces the exposure dose by using the tube voltage lower than before, while not deteriorating the CNR in the reconstructed image.

[Patent Document 1]

Japanese Unexamined Patent Application Publication No. 2004-073865

DISCLOSURE OF THE INVENTION

Problem to be Solved by the Invention

However, the X-ray CT apparatus disclosed in the patent document 1 actually optimizes the X-ray condition focusing on the image SD value, and does not study sufficiently the relationship between the contrast (here, an absolute value of the CT value difference) or the CNR, and the X-ray condition. By way of example, since the contrast between internal organs is not necessarily dependent on the tube voltage extensively, the use of tube voltage lower than before, while preventing the image SD value from increasing, is not necessarily effective for the CNR enhancement.

In addition, it is not clearly described how the processing actually proceeds for allowing the exposure dose to be reduced while keeping the CNR. The CNR to be achieved is different depending on the size of the diagnostic object, and therefore, the X-ray condition to be set is also different. However, this point is not discussed in the document either.

In view of the problems above, an object of the present invention is to provide an X-ray CT apparatus having a function to decide the X-ray condition that realizes an appropriate CNR for identifying the diagnostic object.

Means to Solve the Problem

In order to achieve the object above, the X-ray CT apparatus according to the present invention is configured as the following. The X-ray CT apparatus includes; an X-ray tube for producing an X-ray to be irradiated to an object, an X-ray detector being disposed at a position opposed to the X-ray tube so as to place the object between the X-ray tube and the X-ray detector, for detecting the X-ray that has passed through the object, a scanner rotor being equipped with the X-ray tube and the X-ray detector for rotating around the object, an operating means for inputting and setting information necessary for a scanogram imaging and a scan imaging, and for carrying out an operation, an imaging condition decision means for deciding an imaging condition upon scanning, based on scanogram projection data of the object detected by the X-ray detector, and a scan means for doing a scan under the imaging condition that is decided by the imaging condition decision means, and the X-ray CT apparatus reconstructs a tomographic image of the object based on a transmitted X-ray dose that is scanned by the scan means and detected by the X-ray detector, wherein, the imaging condition decision means includes, a storage means for storing a standard imaging condition, an object three-dimensional model generating means for analyzing the scanogram projection data and generating an object three-dimensional model, a diagnostic object size setting means for setting a diagnostic object size of the object by the operating means, and an X-ray condition calculating means for calculating an X-ray condition to obtain a contrast to noise ratio for identifying the diagnostic object, from the diagnostic object size being set, the object three-dimensional model, and the standard imaging condition.

The X-ray CT apparatus further includes, a display means for displaying expected values of evaluation index upon imaging under the X-ray condition (e.g., a tube voltage or a tube current time product) finally calculated by the X-ray condition calculating means, and under another X-ray condition being different from the X-ray condition described above, and an X-ray condition selection means for selecting the X-ray condition being associated with the expected values of evaluation index displayed on the display means. The expected values of the evaluation index may include at least one of the followings; a tube voltage, a tube current, an exposure dose, an assumed contrast value of the diagnostic object, a contrast to noise ratio, an image SD value, an identifiable size of the diagnostic object, and X-ray tube power consumption.

The X-ray CT apparatus further includes, an X-ray condition selection means for selecting the X-ray condition being associated with the expected values of the evaluation index that are displayed on the display means. In the X-ray CT apparatus according to the present invention, the X-ray condition calculating means may take various kinds of aspects being exemplified in the following.

The X-ray condition calculating means includes, a first image SD predictive value calculating means for calculating a first image SD predictive value, an image SD value being achieved at each slice position within an imaging region set by the operating means, when using a standard tube voltage and a standard tube current time product constituting the standard imaging condition, a reference slice position calculating means for calculating a reference slice position that maximizes the first image SD predictive value in a specific slice positional range set within the imaging range, a contrast to noise ratio calculating means for calculating a contrast to noise ratio for identifying the diagnostic object from the diagnostic object size being set, a first image SD reference value calculating means for calculating a first image SD reference value at the standard tube voltage, by using the contrast to noise ratio calculated by the contrast to noise ratio calculating means, a first tube current time product calculating means for calculating a first tube current time product for achieving the first image SD reference value, a first tube voltage calculating means for calculating a first tube voltage that allows the image SD predictive value to be equal to or less than a predetermined upper limit, when the first tube current time product is used at the reference slice position, a second image SD reference value calculating means for calculating a second image SD reference value that is achieved by the first tube voltage and the first tube current time product at the reference slice position, a second image SD predictive value calculating means for calculating a second image SD predictive value that is achieved by the first tube voltage and the first tube current time product at each slice position within the imaging region, and a second tube current time product calculating means for calculating a second tube current time product for achieving the second image SD reference value at each slice position within the imaging region, from the first tube voltage, the second image SD predictive value and the second image SD reference value, wherein, the first tube voltage and the second tube current time product are assumed as the X-ray condition.

An example of specific means of the contrast to noise ratio calculating means and the first image SD reference value calculating means is as the following:

(1) The contrast to noise ratio calculating means is a means to calculate the contrast to noise ratio, from a function of a relationship between the diagnostic object size and a contrast to noise ratio enabling identification of the diagnostic object.

(2) The first image SD reference value calculating means is a means to calculate the first image SD reference value, by dividing an assumed contrast value at the standard tube voltage of the diagnostic object stored in the storage device, by the contrast to noise ratio calculated by the contrast to noise ratio calculating means.

The X-ray condition calculating means includes, a true positive fraction and false position fraction setting means for setting a true positive fraction and a false positive fraction in the diagnostic object of the object being set by the diagnostic object size setting means, a contrast to noise ratio calculating means for calculating a contrast to noise ratio for identifying the diagnostic object from the diagnostic object size being set, a slice position calculating means for calculating a reference slice position that maximizes an image SD value under an identical imaging condition in the object three-dimensional model, an image SD value calculating means for calculating an image SD value at the reference slice position, from an assumed contrast value and the contrast to noise ratio calculated by the contrast to noise ratio calculating means, a tube current time product calculating means for calculating a first tube current time product that achieves the image SD value calculated in the image SD value calculating means, a tube current time product correction coefficient calculating means for calculating a tube current time product correction coefficient to keep the contrast to noise ratio approximately constant irrespective of the tube voltage under the condition of the first tube current time product, a tube current time product correction means for correcting the first tube current time product using the tube current time product correction coefficient, and a tube voltage calculating means for calculating a tube voltage that minimizes an exposure dose under the condition where power consumed by the X-ray tube is equal to or less than a reference value of X-ray tube power which constitutes the standard imaging condition, wherein the tube voltage calculated by the tube voltage calculating means and the tube current time product being corrected by the tube current time product correction means are assumed as the X-ray condition.

Example of the contrast to noise ratio calculating means, the assumed contrast value, the tube current time product calculating means, and the tube current time product correction coefficient calculating means are as the following:

(3) The contrast to noise ratio calculating means is a means to calculate the contrast to noise ratio, from the relationship between the diagnostic object size and the contrast to noise ratio enabling identification of the diagnostic object, the relationship between the true positive fraction and the false positive fraction, and the relationship between the contrast to noise ratio enabling identification and the false positive fraction.

(4) The assumed contrast value is obtained from the relationship between an adult object average size at the standard tube voltage of the standard imaging condition, and a contrast effect according to the diagnostic object size of the object that is normalized by the average value.

(5) The tube current time product calculating means is a means to obtain the first tube current time product from the relationship between the image SD value and the tube current time product in the object size.

(6) The tube current time product correction coefficient calculating means is a means to obtain the correction coefficient from the relationship between the tube voltage and the normalized contrast to noise ratio in the object size being predetermined.

The X-ray condition calculating means includes, a slice position calculating means for calculating a reference slice position that maximizes an image SD value under an identical imaging condition in the object three-dimensional model, a target image SD value setting means for inputting and setting a target image SD value from the operating means, a diagnostic object size calculating means for calculating a contrast to noise ratio enabling identification of the diagnostic object of the object from an assumed contrast value at the reference slice position and the target image SD value, so as to calculate a diagnostic object size, a diagnostic object size determination input means for accepting whether or not the diagnostic object size being calculated is appropriate as an actual diagnostic object size, a tube current time product calculating means for calculating a first tube current time product that satisfies the target image SD value in the diagnostic object size at the reference slice position, when it is determined that the diagnostic object size being calculated is appropriate, an image SD value adjusting means for adjusting the target image SD value in such a manner that the diagnostic object size is rendered to be appropriate, when it is determined that the diagnostic object size being calculated is not appropriate, a tube current time product correction coefficient calculating means for calculating the tube current time product correction coefficient that keeps the contrast to noise ratio to be approximately constant irrespective of the tube voltage under the condition of the first tube current time product, a tube current time product correction means for correcting the first tube current time product by the current product correction coefficient, and a tube voltage calculating means for calculating a tube voltage that minimizes the exposure dose under the condition where power consumed by the X-ray tube is equal to or less than a reference value of an X-ray tube power which constitutes the standard imaging condition, wherein, the tube voltage calculated by the tube voltage calculating means and the tube current time product corrected by the tube current time product correction means are assumed as the X-ray condition.

An example of the assumed contrast value, the tube current time product calculating means, and the tube current time product correction coefficient calculating means is as the following:

(7) The assumed contrast value is calculated based on the diagnostic object size calculated by the diagnostic object size calculating means and the reference slice position.

(8) The tube current time product calculating means is a means to obtain the tube current time product, from the relationship between the image SD value and the tube current time product at the reference slice position in the diagnostic object size being predetermined.

(9) The tube current time product correction coefficient calculating means is a means to obtain the correction coefficient, from the relationship between the tube voltage and a normalized contrast to noise ratio in the object size being predetermined.

The X-ray condition calculating means includes; a desired slice position designating means for designating a desired slice position by the operating means, a false positive fraction setting means for setting a false positive fraction of the diagnostic object of the object being set by the diagnostic object size setting means, a desired slice position image SD value predicting means for calculating an image SD predictive value at the desired slice position from the assumed contrast value and the object three-dimensional model at the desired slice position, a contrast to noise ratio calculating means for calculating a contrast to noise ratio for identifying the diagnostic object at the desired slice position being designated, from the image SD predictive value at the desired slice position and the assumed contrast value, an image SD predictive value feasibility determination means for determining whether or not the image SD predictive value at the desired slice position is feasible, a false positive fraction and diagnostic object size adjusting means for adjusting the false positive fraction and the diagnostic object size so as to achieve a feasible image SD predictive value, when it is determined that the image SD predictive value is unfeasible at the desired slice position, and a contrast to noise ratio determining means for determining whether or not the contrast to noise ratio calculated by the contrast to noise ratio calculating means is applicable to all the slice positions, when it is determined that the image SD predictive value is feasible, wherein, when it is determined that the contrast to noise ratio is applicable to all the slice positions, the X-ray condition calculating means further includes; a tube current time product calculating means for calculating a first tube current time product to obtain an image SD predictive value at the desired slice position, a tube current time product correction coefficient calculating means for calculating a tube current time product correction coefficient for keeping the contrast to noise ratio to be approximately constant irrespective of the tube voltage under the condition of the first tube current time product, a tube current time product correction means for correcting the first tube current time product by the tube current time product correction coefficient, and a tube voltage calculating means for calculating a tube voltage that minimizes the exposure dose under the condition where the power consumed by the X-ray tube is equal to or less than the reference value of the X-ray tube power that constitutes the standard imaging condition, wherein, the tube voltage calculated by the tube voltage calculating means and the tube current time product corrected by the tube current time product correction means are assumed as the X-ray condition.

An example of the tube current time product calculating means and the tube current time product correction coefficient calculating means is as the following.

(10) The tube current time product calculating means is a means to obtain the first tube current time product, from the relationship between the image SD value and the tube current time product at the desired slice position in the object size being predetermined.

(11) The tube current time product correction coefficient calculating means is a means to obtain the correction coefficient from the relationship between the tube voltage and the normalized contrast to noise ratio in the object size being predetermined.

Furthermore, the slice position where the contrast to noise ratio calculated by the contrast to noise ratio calculating means cannot be achieved is highlighted by the display means.

When the contrast to noise ratio determination means determines that the contrast to noise ratio calculated by the contrast to noise ratio calculating means is not applicable to all the slice positions, there is provided an applicability to all the slice positions determination means for determining whether or not the image SD predictive value at the slice position being designated is applicable to all the slice positions. When the applicability to all the slice positions determination means determines that the image SD predictive value is applicable to all the slice positions, there are provided a second tube current time product calculating means for calculating a second tube current time product that satisfies, irrespective of the slice position, the image SD predictive value at the desired slice position and an object size comparing means for comparing the object size as to each slice position, and the object size at the desired slice position being designated. Here, the tube current time product correction coefficient calculating means calculates a tube current time product correction coefficient so as to keep the contrast to noise ratio to be approximately constant irrespective of the tube voltage under the condition of the second tube current time product, when it is determined that the object size at the desired slice position being designated is equal to or less than the object size at the scan position in the object size comparing means, and the tube current time product correcting means corrects the second tube current time product by the correction coefficient, and the tube voltage calculated by the tube voltage calculating means and the tube current time product being corrected by the tube current time product correction means are assumed as the X-ray condition.

An example of the second tube current time product calculating means and the tube current time product correction coefficient calculating means is as the following:

(12) The second tube current time product calculating means is a means to obtain the second tube current time product from the relationship between the image SD value and the tube current time product at the desired slice position in the predetermined diagnostic object size of the object.

(13) The tube current time product correction coefficient calculating means is a means to obtain the correction coefficient from the relationship between the tube voltage and the normalized contrast to noise ratio in a predetermined size of the diagnostic object of the object.

When the object size comparing means determines that the object size at the slice position is larger than the object size at the slice position being designated, the X-ray condition calculating means is provided with a third tube current time product calculating means for calculating a third tube current time product that satisfies for each slice position the image SD predictive value at the desired slice position, under the tube voltage being calculated by the tube voltage calculating means, wherein the tube current time product correction coefficient calculating means calculates the tube current time product correction coefficient for keeping the contrast to noise ratio to be approximately constant irrespective of the tube voltage under the condition of the third tube current time product, and the tube current time product correction means corrects the third tube current time product by the correction coefficient, and the tube voltage calculated by the tube voltage calculating means and the tube current time product corrected by the tube current time product correction means are assumed as the X-ray condition.

An example of the third tube current time product calculating means and the tube current time product correction coefficient calculating means is as the following.

(14) The third tube current time product calculating means is a means to obtain the third tube current time product from the relationship between the image SD value and the tube current time product at the desired slice position in the object size.

(15) The tube current time product correction coefficient calculating means is a means to obtain the correction coefficient from the relationship between the tube voltage and the normalized contrast to noise ratio in the object size.

When the image SD predictive value at the slice position being designated cannot be applied to all the slice positions, there are provided a fourth tube current time product calculating means for calculating a fourth tube current time product that satisfies the image SD value at the designated slice position, an exposure dose and X-ray tube power at the designated slice position calculating means for calculating the exposure dose and the X-ray power by using the fourth tube current time product at the slice position being designated, and a second tube voltage calculating means for calculating a second tube voltage that minimizes the exposure dose under the condition that the X-ray tube power calculated by the calculating means is equal to or less than the reference value of the X-ray tube power which constitutes the standard imaging condition, wherein, the second tube voltage and the fourth tube current time product are assumed as the X-ray condition.

The X-ray condition calculating means includes, multiple regions of interest (ROI) setting means for setting a scan area by the operating means and for setting multiple regions of interest within the area, a multiple false positive fractions setting means for setting false positive fractions of diseases existing respectively in multiple diagnostic object sizes which are set by the diagnostic object size setting means respectively in the multiple regions of interest set by the multiple ROI setting means, a contrast to noise ratio calculating means for calculating a contrast to noise ratio for identifying the diagnostic object from each of the diagnostic object sizes of the multiple regions of interest being set, a slice position calculating means for calculating a slice position that maximizes an image SD value for each of the regions of interest being set in the object three-dimensional model, an image SD value calculating means for calculating the image SD value at the slice position calculated by the slice position calculating means, from an assumed contrast value and the contrast to noise ratio calculated by the contrast to noise ratio calculating means, a tube current time product calculating means for calculating a tube current time product to achieve the image SD value calculated by the image SD value calculating means, a tube current time product correction coefficient calculating means for calculating a tube current time product correction coefficient to keep the contrast to noise ratio to be approximately constant irrespective of a tube voltage, under the condition of the tube current time product calculated by the tube current time product calculating means, a tube current time product correction means for correcting the tube current time product calculated by the tube current time product calculating means, using the tube current time product correction coefficient, and a tube voltage calculating means for calculating the tube voltage that minimizes an exposure dose under the condition where power consumed by the X-ray tube is equal to or less than a reference value of X-ray tube power that constitutes the standard imaging condition, wherein, the tube voltage calculated by the tube voltage calculating means and the tube current time product corrected by the tube current time product correction means are assumed as the X-ray condition.

An example of the tube current time product calculating means and the tube current time product correction coefficient calculating means is as the following.

(16) The tube current time product calculating means is a means to obtain the tube current time product from the relationship between the image SD value and the tube current time product in the object size.

(17) The tube current time product correction coefficient calculating means is a means to obtain the correction coefficient from the relationship between the tube voltage and the normalized contrast to noise ratio in the object size.

The X-ray condition calculating means includes a true positive fraction and a false positive fraction setting means for setting a true positive fraction and a false positive fraction of the diagnostic object of the object set by the diagnostic object size setting means, a contrast to noise ratio calculating means for calculating the contrast to noise ratio for identifying the diagnostic object from the diagnostic object size being set, an image SD value calculating means for calculating an image SD value that satisfies the assumed contrast value and the contrast to noise ratio calculated by the contrast to noise calculating means, for each slice plane existing within a specific slice positional range, and a tube current time product calculating means for calculating the tube current time product that satisfies the image SD value in the diagnostic object size for each slice plane at the tube voltage set as the standard imaging condition, wherein, the tube voltage being set and the tube current time product being calculated by the tube current time product calculating means are assumed as the X-ray condition.

EFFECT OF THE INVENTION

The present invention is configured in such a manner that scanogram projection data of the object is analyzed to generate a three-dimensional model of the object, an X-ray condition for obtaining a contrast to noise ratio to identify the diagnostic object is calculated based on the diagnostic object size of the object, the object three-dimensional model, and the preset standard imaging condition, and the scan is done under the X-ray condition being calculated. With this configuration, the X-ray condition can be decided, which allows an acquisition of an appropriate CNR for identifying the diagnostic object. Consequently, it is possible to provide an X-ray CT apparatus that is able to obtain a tomographic image, with an image quality necessary and sufficient for the diagnosis.

BEST MODE FOR CARRYING OUT THE INVENTION

Hereinafter, preferred embodiments of the X-ray CT apparatus according to the present invention will be explained in detail, with reference to the accompanying drawings. The present invention decides in advance an X-ray condition for obtaining an appropriate contrast to noise ratio to identify the diagnostic object before starting a scan, and the scan is done under the decided X-ray condition. The present invention is applicable to any scan mode (axial scan and spiral scan) and any slice type (single-slice and multi-slice). Here, an explanation will be made as to the case where the present invention is applied to the X-ray CT apparatus of the multi-slice type and spiral scan mode.

FIG. 2 is an overall schematic view of the X-ray CT apparatus to which the present invention is applied, and FIG. 1 illustrates its overall configuration. The X-ray CT apparatus as shown in FIG. 2 irradiates the object with X-rays to collect transmitted X-ray data of the object, and subjects the collected X-ray data to reconstructing computation to obtain a tomographic image. The X-ray CT apparatus is made up of a scanner gantry 1 for collecting the X-ray data that is obtained by irradiating the object with X-rays and allowing the X-rays to pass therethrough, a bed 2 equipped with a movable top panel 4 to place the object thereon, and a console 3 equipped with an operating device 6 and a display device 5 for configuring various operational settings and for reconstructing and displaying the X-ray tomographic image based on the X-ray data being collected, and the like.

As shown in FIG. 1, the scanner gantry 1 includes an X-ray tube 8 for producing X-rays, being controlled by an X-ray controller 7. The X-rays emitted from the X-ray tube 8 form, for example, a pyramidal X-ray beam, i.e., a corn beam X-ray, by a collimator 10 that is controlled by a collimator controller 9, and the object 17 is irradiated with this corn beam X-ray, which passes through the object 17, to be incident on an X-ray detector 11.

As shown in FIG. 3, the X-ray detector 11 includes multiple X-ray detector elements 18, which are arranged two-dimensionally, in the channel direction and in the row direction. These X-ray detector elements 18 are made up of, for example, a combination of scintillator and photodiode, and form a shape, as a whole, of cylindrical surface or a polygonal line with respect to the channel direction to constitute an X-ray incident plane. By way of the example, the channel number i ranges approximately from 1 to 1,000 and the row number j ranges approximately from 1 to 1,000. A spread angle of the corn beam X-ray in the channel direction, which corresponds to the channel array direction of the X-ray detector 11, i.e., a fan angle, is $\alpha$, and a spread angle of the corn beam X-ray in the row direction, which corresponds to the row array direction of the X-ray detector 11, i.e., a corn angle, is $\gamma$. The X-ray detector 11 is connected to a data collector 12, and this data collector 12 collects detection data from individual X-ray detector elements 18 of the X-ray detector 11.

The components described above, from the above X-ray controller 7 to the data collector 12, are mounted on a rotor plate 13 of the scanner gantry 1. The rotor plate 13 rotates around the object 17 by a drive force transmitted via a drive force transmitter system 16 from a rotor plate driving device 15, which is controlled by a rotation controller 14.

As shown in FIG. 1, the bed 2 provided with the movable top panel 4 placing the object 17 thereon is configured in such a manner that the bed controller 20 controls a bed vertical transfer device 21 to set the bed at an appropriate height, and the bed controller 20 also controls a top panel transfer device 22 to move the top panel 4 back and forth, so that the object 17 is brought in and taken out of the X-ray irradiation space (opening) 26 of the scanner gantry 1.

As shown in FIG. 4, in the scanner gantry 1 configured as described above, after the object 17 placed on the top panel 4 of the bed 2 is brought into the opening 26 of the scanner gantry 1, the object 17 is irradiated with the corn beam X-ray, whose corn angle $\gamma$ has been adjusted by the opening width of the collimator 10. Then, the X-ray image of the object 17 which is irradiated with the corn beam X-ray is projected on the X-ray detector 11, and the X-ray detector 11 detects the X-rays that passed through the object 17.

The console 3 shown in FIG. 1 is provided with a system controller 19 for controlling the overall system of the X-ray CT apparatus according to the present invention, and this system controller 19 is connected to the scanner gantry 1 and the bed 2. Specifically, this system controller 19 controls the X-ray controller 7, the collimator controller 9, the data collector 12, the rotation controller 14 within the scanner gantry 1, and the bed controller 20 within the bed 2.

Data collected by the data collector 12 is inputted into the image reconstruction device 23 according to the control by the system controller 19. At the time of scanogram imaging, the image reconstruction device 23 uses scanogram projection data (object perspective data) collected by the data collector 12 to generate a scanogram image, and at the time of scanning, the projection data of multiple views being collected by the data collector 12 is used to perform CT image reconstruction.

The scanogram image generated by the image reconstruction device 23, the CT image being reconstructed, various data, and programs and the like to implement functions of the X-ray CT apparatus, are stored in a storage device 24 connected to the system controller 19. The storage device 24 further stores a standard imaging condition. The standard imaging condition indicates an imaging condition that is recommended depending on a physical frame and a part to be imaged of the object 17. The storage device further stores data and the like necessary for calculation in the scan planning device 25, which will be described below. The system controller 19 is connected each of the display device 5 and the operating device 6, and the display device 5 displays the reconstructed image outputted from the image reconstruction device 23 and various information handled by the system controller 19.

An operator manipulates the operating device 6, which is provided with an input means for inputting various directives and information and the like into the system controller 19. The operator manipulates the X-ray CT apparatus according to the present invention interactively by using the display device 5 and the operating device 6.

Furthermore, the system controller 19 is connected to the scan planning device 25 being a critical portion of the present invention, and the scan planning device 25 decides the imaging condition, in advance, before the start of scanning, by using the directive inputted by the operator via the operating device 6 and the scanogram image read out from the storage device 24. Specifically, the scanogram image read out from the storage device 24 is displayed on the display device 5, and the operator designates on the scanogram image of the object being displayed, the coordinate of a position for reconstructing the CT image (hereinafter, referred to as "slice position") by using the operating device 6, thereby enabling the setting of the slice position. Information of the slice position being set here is stored in the storage device 24 and also used to set the X-ray dose control condition and the like.

The X-ray CT apparatus according to the present invention performs various preparatory operations for deciding the imaging condition, before doing a scan for obtaining the CT image of the object. These preparatory operations include imaging of a scanogram image for setting an imaging position of the object, an analysis of the scanogram data obtained by the imaging, and decision of an optimum irradiated X-ray condition as the imaging condition based on the analysis. These preparatory operations are carried out under the control of the system controller 19.

Main components involved in the preparatory operations include, the system controller 19, scan planning device 25, operating device 6, display device 5, X-ray tube 8, and X-ray detector 11, and the like as shown in FIG. 1. In particular, the analysis of the scanogram data and the decision of the optimum irradiated X-ray condition as the imaging condition based on the analysis are significant functions of the scan planning device 25, which is connected to the system controller 19 (imaging condition decision means).

In these preparatory operations, firstly, in order to obtain the scanogram image (perspective image obtained from one direction for planning the scanning range), there are entered via the operating device 6, the X-ray condition mainly such as setting values of the X-ray tube voltage (a voltage applied between the anode and cathode of the X-ray tube 8) and the X-ray tube current (a current flowing between the anode and cathode of the X-ray tube 8). Then, the top panel 4 placing the object 17 thereon and the rotor plate 13 are relatively moved along the body axis of the object 17 without rotating the rotor plate 13, and imaging of the scanogram image is performed. Then, the scanogram projection data and the scanogram image data are stored in the storage device 24. A part of the functions of the image reconstruction device 23 is used to subject the scanogram projection data to a two-dimensional filtering process in the channel direction and in the view direction, whereby the scanogram image data is generated.

The scan planning device 25 analyzes the scanogram projection data for modeling an estimated cross section at an arbitrary position along the body axis of the object, in a form of an elliptic cross section having an X-ray absorption coefficient equivalent to water, for instance. This model becomes a three-dimensional type model (hereinafter, described as "object three-dimensional model"), in which the long-axis length and short-axis length of the elliptic cross section vary depending on the position along the body axis of the object (hereinafter, described as "z-position"). The storage device 24 stores the data of this object three-dimensional model.

The scan planning device 25 calculates a recommended tube voltage and a series of tube current value, i.e., variation pattern of the tube current, which changes over time in accordance with the variation of the object sectional shape during scanning at the recommended tube voltage, based on the diagnostic object size input by the operating device 6, set values of the tube voltage and tube current, the X-ray collimation condition, the time per one rotation of the scanner (hereinafter, described as "scan time"), and the data of the object three-dimensional model generated by the scan planning device 25. The scan planning device 25 having the above functions is a significant constitutional element of the present invention, and with those functions, an optimum X-ray condition during scanning is decided (X-ray condition calculating means).

FIG. 5 is an operational flowchart showing a series of preparatory operations that are carried out prior to scanning, in order to decide the optimum X-ray condition. Hereinafter, with reference to the operational flowchart, a detailed explanation will be given as to the steps for deciding the X-ray condition.

(1) Image Scanogram (Step S100)

A scanogram of the object 17 is imaged. A procedure to image the scanogram of the object 17 is basically the same as the procedure to take a CT image by scanning. The object 17 is irradiated with X-rays from a fixed direction, for instance, from the backside of the object 17, without rotating the rotor plate 13 of the scanner gantry 1. Then, the X-rays passed through the object 17 are detected by the X-ray detector 11, and the detection data is captured, whereby the scanogram projection data is obtained.

The data collector 12 collects the detection data detected by the X-ray detector 11 to obtain the scanogram projection data, and the scanogram projection data is transmitted to the image reconstruction device 23 from the data collector 12 via the system controller 19. Then, the image reconstruction device 23 generates the scanogram image and displays it on the display device 5. The scanogram image obtained at this stage is an image viewed from the front side of an image, which is generated by the X-rays that passed through along the fixed direction, e.g., from the back side to the front side. This scanogram image is utilized for setting a slice position (CT image reconstruction position) of the object 17 upon scanning. The scanogram projection data is not only used for generating the scanogram image, but also utilized for deciding an optimum X-ray irradiated imaging condition upon scanning, which is a particular feature of the present invention.

(2) Input Imaging Condition (Steps S110, S120, and S130)

The operator refers to the scanogram image displayed on the display device 5 and inputs as the imaging condition, a top panel moving pitch, a scanning start position zs, and scanning end position ze. Here, since assumption of zs≦ze will not cause any loss of generality, it is assumed as zs≦ze in the following. By using these input data items, the scan planning device 25 decides a range for capturing a CT image of the object 17, a slice position z, a phase angle of the X-ray tube 8 (a phase angle of the rotor plate 13) β. Here, the scanning start position zs and the scanning end position ze respectively indicate the z position of an initial CT image, and the z position of a final CT image, among the images obtained by a series of scanning.

(3) Input Other Imaging Condition (Step S140)

The operator inputs the imaging condition, from the operating device 6, such as a standard tube voltage, a standard tube current, a scan time, X-ray collimation condition, a type of reconstruction filter function, an FOV size, a slice thickness, and a window condition.

(4) Input Specific Slice Positional Range and Diagnostic Object Size (Step S150)

The operator inputs from the operating device 6, the start position zss and the end position zse of the imaging range particularly focused, and the size d_o of the diagnostic object (for example, contrast-enhanced liver cell cancer). It is to be noted here that zs≦zss≦zse≦ze. When the input of zss is skipped, zss=zs is set automatically, and when the input of zse is skipped, zse=ze is set automatically. In addition, as the size d_o of the diagnostic object, a diameter of the circle having an area equivalent to the diagnostic object (equivalent diameter) is inputted, for instance.

(5) Analyze Scanogram Data and Generate 3D Model of the Object (Steps S160 and S170)

The scan planning device 25 analyzes the scanogram projection data and generates the three-dimensional model of the object 17. This three-dimensional model of the object is an approximation of each cross section of the object 17 in association with the z-position, in a form of an elliptic cross section having the X-ray absorption coefficient equivalent to water. Since the patent document 1 and the Japanese Unexamined Patent Application Publication No. 2001-276040 disclose this approximation method, the explanation thereof will not be made here.

(6) Calculate Image SD Predictive Value at Standard Tube Voltage and Standard Tube Current (Step S180)

When the standard tube voltage xv_ref and standard current time product (a product of the tube current value and the scan time) i_ref are used, a predictive value SD_ref (z, xv_ref, i_ref) of an image SD value of the CT image is calculated, the CT image being obtained at an arbitrary slice position z, within the range from the scan start position zs to the scan end position ze (first image SD predictive value calculating means). Also for this predictive calculation method, the method disclosed in the patent document 1 and the Japanese Unexamined Patent Application Publication No. 2001-276040 can be applied, to the sectional model, the standard tube voltage xv_ref, and the standard current time product i_ref at each slice position z. Therefore, the explanation of the predictive value calculation method will not be made here.

(7) Calculate a Maximum Value of the Image SD Predictive Value and the Slice Position within the Specific Slice Positional Range (Step S190)

The maximum value MAX_SD_ref of the SD_ref(z, xv_ref, i_ref) that is predicted in step S180 within the specific slice positional range (zss≦z≦zse), and the slice position z_MAXSD (reference slice position) where the image SD value becomes MAX_SD_ref are obtained (slice position calculating means for calculating a slice position where the image SD predicted value is the maximum).

(8) Calculate CNR Enabling Identification of the Diagnostic Object (Step S200)

A CNR is obtained which enables identification of the diagnostic object from the diagnostic object size d_o inputted in step S150 (contrast-to-noise ratio calculating means). As shown in FIG. 6, a function CNR_det_func of the relationship between the diagnostic object size d and the CNR enabling identification is obtained in advance by experiment, and a targeted contrast to noise ratio enabling identification CNR_det is obtained according to the following formula:

$$CNR\_det = CNR\_det\_func(d\_o) \quad \text{(Formula 1)}$$

Here, the function CNR_det_func is typically expressed by the next formula:

$$CNR\_det\_func(x) = a \times x - b \quad \text{(Formula 2)}$$

It is to be noted here that a and b are real numbers, and a>0, b>0.

Representation by formula 2 is also possible using a polynomial. For this case, it is expressed as:

$$CNR\_det\_func = a + b^*x + c^*x^2 + \ldots + n^*x^n \quad \text{(Formula 2')}$$

Here, a, b, c, and n are real numbers.

In addition, the relationship between the diagnostic object size d_o and the CNR enabling identification may be held in the storage device as a data table as shown in FIG. 1. This data table may be disclosed to the operator, allowing the operator to make desired modifications to the data table. For this case, it is desirable that an optimum approximate curve is generated automatically based on the modified data, by subjecting the discrete data to the spline interpolation, or the like.

TABLE 1

DATA TABLE OF DIAGNOSTIC OBJECT SIZE AND CNR ENABLING IDENTIFICATION

| Diagnostic object size | d_o1 | d_o2 | ... | d_oN |
|---|---|---|---|---|
| CNR enabling identification | CNR_1 | CNR_2 | ... | CNR_N |

(9) Correct CNR Enabling Identification, Based on Slice Thickness and Window Condition (Steps S201 to S204)

Here, the CNR enabling identification calculated in step S200 is corrected based on the information of the slice thickness and the window condition set in step S140. Specifically, the correcting process is performed according to the procedure as shown in FIG. 7.

(9-1) Step S201

A diagnostic object effective diameter d_eff is calculated from the slice thickness and the diagnostic object size d.

When the diagnostic object is assumed as a sphere, the slice becomes thicker, the apparent size of the sphere becomes smaller. Therefore, an effective size of the diagnostic object is obtained here. Typically, it is expressed according to the following formula. When the slice thickness is assumed as Sthick, the formula is:

$$Sthick \le d\_o \quad d\_eff = \frac{Sthick\sqrt{d\_o^2 - Sthick^2} + d\_o^2 \sin^{-1}(Sthick/d\_o)}{2 \cdot Sthick} \quad \text{[Formula 1]}$$

$$Sthick > d\_o \quad d\_eff = \frac{\pi \cdot d\_o}{4}$$

(9-2) Step S202

An influence on the CNR enabling identification is corrected based on the effective diameter d_eff of the diagnostic object. Here, the variation of the effective diameter caused by the slice thickness influences the CNR enabling identification.

As shown in FIG. 8(a), in the graph indicating the relationship between the CNR enabling identification and the diagnostic object size (diameter), when the diagnostic object size is changed from d_o to d_eff, the CNR enabling identification is also changed, and the CNR enabling identification after the correction at this point of time becomes CNR_d_modu1.

(9-3) Step S203

An influence exerted on the contrast of the diagnostic object by the slice thickness and the window condition (window width and window level) is corrected. When the slice thickness and the window condition are changed, an apparent contrast of the diagnostic object is changed. Accordingly, it is necessary to correct the CNR enabling identification appropriately.

FIG. 8(b) is a schematic view showing the rate of change of the apparent CNR enabling identification (CNR_app) of the diagnostic object associated with the variation of the window condition (window width and window level: W_Cond). Typically, it is expressed by the formula 2 and the formula 2', in which CNR_det_func is replaced by CNR_app, and x is replaced by W_Cond. Therefore, when the window condition is taken into account and the CNR enabling identification after the correction is expressed as CNR_d_modu2, it is defined as:

$$CNR\_d\_modu2 = CNR\_d\_modu1 * CNR\_app$$

(9-4) Step S204

As discussed above, according to the procedures from S201 to S203, it is possible to obtain the corrected CNR enabling identification (CNR_d_modu2) considering the slice thickness and the window condition. The correction of the CNR enabling identification according to step S201 to step S204 is not indispensable in the present embodiment. However, the correction considering the slice thickness and the window condition allows the X-ray condition to be set at a higher degree of precision. Hereinafter, the contrast to noise ratio enabling identification CNR_det, which is to be referred to, includes the contrast to noise ratio enabling identification after the correction was made as described above.

(10) Calculate Image SD Reference Value to be Achieved at the Standard Tube Voltage (Step S210)

SD_xv_ref being a reference value of the image SD value to be achieved at the standard tube voltage is obtained according to the following formula, based on the assumed contrast value C_o at the standard tube voltage xv_ref of the diagnostic object, the contrast value being stored in advance in the storage device 24 and CNR_det being obtained in step S200 (first image SD reference value calculating means):

$$SD\_xv\_ref = C\_o / CNR\_det \quad \text{(Formula 3)}$$

(11) Calculate Current Time Product i_ta(z_MAXSD) to Achieve the SD_xv_ref (Step S220)

The tube current time product i_ta(z_MAXSD) is obtained according to the following formula, for achieving the SD_xv_ref being the image SD value at the standard tube voltage xv_ref and at the reference slice position z_MAXSD (first tube current time product calculating means):

$$i\_ta(z\_MAXSD) = i\_ref \times (MAX\_SD\_ref / SD\_xv\_ref)^2 \quad \text{(Formula 4)}$$

(12) Calculate Tube Voltage xv_a Satisfying the Image SD≦the Upper Limit SD_ULIM, and Image SD Value SD_xv_a Predicted at the Slice Position Z_MAXSD (Step S230)

Considering the image quality of the portion other than the identification target, the tube voltage xv_a is obtained, which allows the image SD when the tube current time product is i_ta(z_MAXSD) calculated in the formula 4, to become equal to or less than the upper limit value SD_ULIM. As for the upper limit value SD_ULIM of the image SD, an appropriate value is inputted from the operating device in advance, or alternatively, a recommended value may be set as a default in the storage device 24. Here, it is known that the CNR of the contrast-enhanced target is kept approximately constant irrespective of the tube voltage, under the condition that the tube current is kept unchanged. Therefore, variation of the tube voltage may not adversely affect the diagnosis of the contrast-enhanced target. Accordingly, in calculating the tube voltage xv_a, the predictive function of the image SD value is employed, and the lowest tube voltage xv_a satisfying the following formula is obtained by using the relationship between the tube voltage and the image SD, under the condition that the slice position is z_MAXSD and the tube current time product is i_ta(z_MAXSD) as shown in FIG. 9, the relationship being obtained based on experimental data and the like (first tube voltage calculating means):

$$SD\_ULIM \geqq SD\_func(xv\_a) \quad \text{(Formula 5)}$$

On this occasion, the image SD value predicted at the slice position z_MAXSD is assumed as SD_xv_a. It is to be noted that the relationship between the tube voltage and the image SD is typically expressed as shown in the following formula:

$$SD\_func(x) = c \times x^{-g} \quad \text{(Formula 6)}$$

Here, c and g are real numbers, and c>0 and g>0.

(13) Calculate Image SD Predictive Value when the Tube Voltage is xv_a and the Tube Current Time Product is i_ta (z_MAXSD) (Step S240)

According to the image SD predictive function, the image SD value SD_ref(z, xv_a, i_ta(z_MAXSD)) of the CT image is predicted, which is obtained when the tube voltage xv_a and the tube current time product i_ta(z_MAXSD) are used at each slice position z (second image SD predictive value calculating means).

(14) Calculate Current Time Product i_r(z) for Achieving the Image SD Value SD_xv_a at the Slice Position z (Step S250)

The tube current time product i_r(z) for achieving the image SD value SD_xv_a is obtained according to the following formula, the image SD value being predicted at the slice position z_MAXSD under the condition that the tube voltage is xv_a at each slice position z (second tube current time product calculating means):

$$i\_r(z) = i\_ta(z\_MAXSD) \times (SD\_ref(z, xv\_a, i\_ta(z\_MAXSD)) / SD\_xv\_a)^2$$

The tube current time product i_r(z) and the tube voltage xv_a being obtained according to the above procedure are assumed as a recommended condition of the tube current time product and the tube voltage being calculated in the scan planning device 25.

(15) Display the Relationship of Tube Voltage and Tube Current to Exposure Dose and Image SD Predictive Value (Step S260)

Expected values are calculated, such as the exposure dose (CTDI: Computed Tomography Dose Index), the image SD value, the identifiable size of the diagnostic target, in the case where the imaging is performed, under the aforementioned recommended condition and other conditions, and these values are displayed as options for the operator. By way of example, as to each of the following options <1> to <3>, as shown in FIG. 10, expected values such as the tube voltage, the average tube current (a value obtained by dividing the tube current time product by the scan time), the exposure dose (CTDI), the image SD value, the identifiable size of the diagnostic object, and the like, are displayed (expected values of evaluation index displaying means). Here, it is clearly demonstrated that the option <1> is the recommended condition among those options. It is to be noted that the identifiable size of the diagnostic object can be calculated by using the inverse function of the function CNR_det_func described in the formula 1.

<1> Tube voltage xv_a and current time product i_r(z) are used (recommended condition)

<2> Standard tube voltage xv_ref and current time product i_r(z) are used (only the tube current is optimized)

<3> Standard tube voltage xv_ref and standard current time product i_ref are used (no optimization)

In the aforementioned options <1>, <2>, and <3>, <1> indicates the case where both the tube voltage and the tube current are optimized, <2> indicates the case where only the tube current is optimized and a standard value is used for the tube voltage, and <3> indicates the case where the standard imaging condition is used without optimizing any of the tube voltage and the tube current.

Displaying values as described above makes each of the cases clearly understandable in regard to advantages and disadvantages, and the operator is allowed to choose the imaging condition, taking these advantages and disadvantages into account. Generally, when an X-ray condition is acquired for achieving a CNR appropriate for identifying the diagnostic object, which is the object of the present invention, and scanning is performed under the X-ray condition, the case <1> is the best. However, the options other than <1> may be selected according to decision of a radiologist or the like. Even in such a case, if predicted values are displayed regarding a resultant image quality and the like, it is helpful for making a decision.

(16) Select Imaging Condition (Step S270)

The operator selects the most appropriate condition from the options as described in step S260.

The selection of the condition is performed as the following, for instance: the conditions shown in FIG. 10 are displayed on the display device 5, and a condition to be used is selected out of the conditions being displayed, via an input unit of the operating device 6, for example, by a mouse clicking (X-ray condition selection means).

As discussed above, it is possible to decide the imaging condition that is able to achieve an appropriate CNR for identifying the diagnostic object. It is to be noted here that in order to make the diagnostic object to be identifiable with the minimum exposure dose, the option <1> is the most suitable. However, if it is desired to obtain an image having an image SD value smaller than the option <1> even though there is some increase of exposure dose, the option <2> is selected. On the other hand, if it is considered most appropriate to do scanning under the standard condition to which the operator is empirically accustomed, the option <3> is selected. However, there is a possibility that the option <3> cannot achieve an appropriate CNR, and if the identifiable size being displayed becomes larger than the inputted diagnostic object size, the option <1> or the option <2> may be selected again.

As thus described, when the imaging condition is decided actually, it may be decided based on the experience and the like of the radiologist. Therefore, considering such situation, it is configured such that the imaging condition can be selected in accordance with the usage purpose as described above, and therefore, a flexible system can be established.

The imaging condition decided according to the procedure above is stored in the storage device 24. While doing a scan, the system controller 19 reads out the imaging condition sequentially for each imaging part of the object 17, and controls the imaging condition (the tube voltage and the tube current) during scanning via the X-ray controller 7.

The devices such as the system controller 19, the scan planning device 25, and the operating device 6, for executing the aforementioned functions and processing can be implemented by a configuration that is operated according to computer programs. The configuration is established by combining elements such as a processor, a computer, a memory, a storage device, a register, a timing control, an interrupt, a communication interface, and an I/O signal interface.

The present invention has been explained referring to one embodiment. However, it should be understood that the present invention is not limited to this embodiment, and the disclosed embodiment is susceptible of changes and modifications without departing from the scope of the invention.

As discussed above, the X-ray CT apparatus of the present invention is provided with the scan planning device 25, which allow a scanogram analysis and an object three-dimensional model generation function, in which the three-dimensional model of the object 17 is generated from the scanogram projection data of the object 17, and an optimum imaging condition setting function which calculates a CNR necessary for diagnosis according to the identification target size, and calculates and sets the imaging condition appropriate for the imaging part of the object, based on the three-dimensional model of the object 17. Therefore, it is possible to easily provide an X-ray CT examination that enables an acquisition of an object image with an appropriate image quality.

Next, five other preferred embodiments will be explained with reference to the drawings from FIG. 11. In order to distinguish the five other preferred embodiments from the embodiment having been explained with the operational flow shown in FIG. 5, the example shown in FIG. 5 is assumed as the first embodiment, and the five other embodiments are assumed as the second embodiment, the third embodiment, the fourth embodiment, the fifth embodiment, and the sixth embodiment, in the order explained below.

SECOND EMBODIMENT

FIG. 11 is an operational flowchart showing a series of preparatory operations which are carried out prior to scanning for deciding the aforementioned optimum X-ray condition in the second embodiment. Hereinafter, steps for deciding the X-ray condition will be explained in detail, with reference to this operational flowchart. The present embodiment is different from the first embodiment in the following points; (a) in calculating the CNR enabling identification, a true positive fraction and a false positive fraction are used in addition to the diagnostic object size, (b) a tube current time product mAs is obtained for achieving the CNR enabling identification, by using the relationship between the image SD obtained in advance and the tube current time product mAs, and (c) the tube current time product mAs being obtained is corrected in such a manner that the CNR is kept to be approximately constant irrespective of the tube voltage. By employing the point (a) above, a recommended imaging condition can be calculated based on the CNR enabling identification, taking an interpretation ability of a radiologist into account.

(1) Image Scanogram (Step S300)

A scanogram of the object 17 is imaged. Since imaging of the scanogram is the same as the first embodiment, the details thereof will not be tediously explained.

(2) Set a Scan Area and Input an Imaging Condition (Step S301)

This process is the same as the steps S110, S120, S130, and S140 of the first embodiment, and an operator refers to the scanogram image and sets via the operating device 6, an imaging region (scanning start position zs and scanning end position ze) including the diagnostic object. Here, as the imaging condition of the slice position, a slice thickness, a top panel moving pitch, a scan time, a standard tube voltage, a standard tube current, an X-ray collimation condition, types of reconstruction filter function, an FOV size, a window condition, and the like, are inputted.

(3) Analyze Scanogram Data (Step S302) and Generate an Object 3D Model (Step S303)

Similar to S160 and S170 of the first embodiment, the scan planning device 25 analyzes the scanogram projection data, and generates the object three-dimensional model of the object 17.

(4) Input Diagnostic Object Size d_o, and TPF and FPF (Step S304)

The size of a thing assumed as the diagnostic object (e.g., contrast-enhanced liver cell cancer) is inputted and set via the input unit of the operating device 6. In addition, the operator inputs and sets the true positive fraction and the false positive fraction, serving as a guide for a diagnosis, via the input unit of the operating device 6, the true positive fraction being described as "TPF", indicating a probability that a disease existing in the diagnostic object is properly identified) and a false positive fraction being described as "FPF", indicating a probability that a disease is determined to exist in the diagnostic object, even though such disease does not actually exist therein (TPF and FPF setting means). The size of the diagnostic object is assumed as a diameter r of a circle (circle equivalent diameter) having an area equivalent to the diagnostic object.

(5) Calculate CNR_det that Allows the Diagnostic Object to be Identified (Step S305)

According to the diagnostic object size d_o inputted by the operator in step S304, CNR_det which can identify the diagnostic object is obtained (contrast to noise ratio calculating means). The CNR enabling identification CNR_det is calculated by using a relational chart between the diagnostic object size d_o and the CNR enabling identification as shown in FIG. 12 (a relationship between the diagnostic object size and the contrast to noise ratio enabling identification), a relational chart between the FPF and TPF as shown in FIG. 13(a) (a relationship between the true positive fraction and the false positive fraction), and a relational chart between CNR enabling identification and FPF as shown in FIG. 13(b) (a relationship between the contrast to noise ratio enabling identification and the false positive fraction).

At first, in order to obtain the relationship between the diagnostic object size d_o and the CNR enabling identification as shown in FIG. 12, it is necessary for the operator to input TPF, FPF, d_o, and the like, for instance, to obtain the relationship between FPF and TPF as shown in FIG. 13(a) and the relationship between the CNR enabling identification and FPF as shown in FIG. 13(b) as described below.

An ROC curve (receiver operating characteristic curve) representing the relationship between the FPF and TPF as shown in FIG. 13(a) is calculated by conducting an ROC analysis by using an image with an already-known CNR, for the case where the CNR is made to be variable with respect to each diagnostic target size, and then the result of the calculation is stored in the storage device 24. When the TPF value inputted by the operator in step S304 is T on the ROC curve of FIG. 13(a), the scan planning device 25 calculates FPF=F, corresponding to TPF=T, according to the ROC curve when d_o=r and CNR=a, for instance. Similarly, according to the ROC curve for each different CNR, FPF corresponding to TPF=T is obtained, and the CNR-FPF curve as shown in FIG. 13(b) is generated. Thereafter, on the CNR-FPF curve, CNR_det when FPF=F1, for instance, is calculated as the CNR enabling identification for the diagnostic object size r (see FIG. 12).

The CNR-FPF curve is generated as to various diagnostic object sizes at the time when the operator inputs TPF, and it is stored in the storage device 24. Here, by further defining an FPF value, a relational chart between the diagnostic object size d_o and the CNR enabling identification is generated as shown in FIG. 12. On the basis of the relational chart as shown in FIG. 12, the operator inputs the diagnostic object size d_o associated with the pertinent examination, whereby a CNR_det enabling identification associated with the diagnostic object size d_o can be calculated.

It is to be noted that the ROC curve for each CNR stored in the storage device 24 can be modified according to the radiologist. When the curve is modified according to the radiologist, a data set for conducting the ROC analysis may be stored in the storage device 24, or a data set prepared by the operator may be used.

In step S304, it is alternatively possible to skip inputting TPF and FPF, and default values, such as TPF=0.95 and FPF=0.05, are stored in the storage device 24 in advance. Furthermore, inputting of the diagnostic object size d_o may be skipped. In this case, according to a diagnostic object part or an imaging part, a value is set in advance in the storage device 24, d_o=10 mm for a region of liver, for instance, and this value may be modified by the radiologist. It is to be noted that the relationship between the diagnostic object size d_o and the CNR enabling identification is typically the same as the aforementioned formula 2.

Here, if the radiologist is predesignated, the data set stored in the storage device 24 is called before step S304, and by using the ROC analysis result obtained by the radiologist and the formula 2, a CNR enabling identification is obtained, which is derived from the diagnostic object size set by the radiologist. Consequently, the curve of the calculated formula 2 perfectly coincides with the interpretation ability of the radiologist, whereby it is possible to set a more suitable CNR enabling identification. Setting of the CNR enabling identification according to this method is also applicable to the following embodiments (the third embodiment, the fourth embodiment, and the fifth embodiment) in the similar manner. Furthermore, the CNR enabling identification calculated in step S305 as described above may be corrected, considering the slice thickness and the window condition inputted in step S301, in the similar manner as the steps S201 to S204 (FIG. 7) of the first embodiment.

(6) Calculate Slice Position z_MAXSD2 that Maximizes the Image SD, Under the Identical Imaging Condition in the 3D Model Being Generated (Step S306)

A reference slice position z_MAXSD2 is calculated, which maximizes the image SD under the identical condition within the scan range, from the three-dimensional model of the object 17 generated in step S303 (slice position calculating means). This z_MAXSD2 is calculated by analyzing the projection height of the scanogram (the projection height is associated with X-ray attenuation for each slice; the larger is the projection height, the larger is the X-ray attenuation, and accordingly the image SD becomes larger).

(7) Calculate Image SD(z_MAXSD2) at the Reference Slice Position z_MAXSD2, from the Assumed Contrast Value and CNR_det (Step S307)

In this step, according to the assumed contrast value C_d considering the imaging part, the object size, and the like, and the CNR_det calculated in step S305, SD(z_MAXSD2) being the image SD at the reference slice position z_MAXSD2 is calculated by the following formula 7 (image SD value calculating means):

$$SD(z\_MAXSD2)=C\_d/CNR\_det \quad \text{(Formula 7)}$$

Assuming a contrast of the liver area, for instance, the assumed contrast value C_d indicates an absolute value of a CT value difference between the liver cell cancer as a diagnostic object and the liver substance. Here, the assumed contrast value of the liver becomes larger in proportion to the density of contrast agent administered to a patient. Furthermore, the larger is the object size, the smaller the assumed contrast value is.

FIG. 14 is a schematic diagram showing an assumed contrast value when the standard tube voltage is xv_ref, in association with the object size, which is normalized by an average size of adult object Pat_ave. When the object size at z_MAXSD2 can be calculated as Pat_R, based on the scanogram analysis data, it is indicated that the normalized assumed contrast value is c(R). Calculation of the assumed contrast value $\Delta HU\_ref$ is actually expressed by the formula 8, for instance:

$$\Delta HU\_ref=(HU\_dia/HU\_init) \times c(R) \quad \text{(Formula 8)}$$

Here, HU_init represents a contrast agent density that is used to calculate a normalized contrast effect, and HU_dia represents a contrast agent density that is actually used in clinical status. This HU_ref is used as the assumed contrast effect C_d in the formula 7.

The aforementioned assumed contrast value is stored in advance in the storage device 24, in association with a diagnostic object portion, an imaging part, an object physical frame, and the like.

(8) Calculate mAs(z_MAXSD2) Satisfying SD(z_MAXSD2) at the Reference Slice Position z_MAXSD2 when the Object Size is L (Step S308)

According to the relationship between the image SD when the object size is L, and the tube current time product mAs as shown in FIG. 15, the tube current time product mAs(z_MAXSD2) associated with the image SD=SD(z_MAXSD2) is calculated (current time product calculating means). Here, the tube voltage condition of the curve of the image SD—current time product mAs is assumed as 120 kV, for instance (hereinafter, referred to as standard tube voltage xv_ref).

The relational chart between the image SD and the tube current time product mAs as shown in FIG. 15 is used among those stored in the storage device 24 in advance as to each object size. As the data necessary for generating the relational chart, the data obtained by imaging water phantoms of various sizes by the X-ray CT apparatus to be employed, or data generated based on simulation data may be used.

(9) Calculate mAs Correction Coefficient and Correct mAs for Keeping the CNR Approximately Constant Irrespective of the Tube Voltage, on the Basis of the Relationship Between the Tube Voltage and Normalized CNR when the Object Size is L, Under the Condition of mAs(z_MAXSD2) (step S309)

Under the condition of the tube current time product mAs (z_MAXSD2) calculated in step S308, on the basis of the relational chart between the tube voltage and the normalized CNR when the object size is L as shown in FIG. 16, mAs correction coefficient λ is calculated for keeping the CNR approximately constant irrespective of the tube voltage (tube current time product correction coefficient calculating means). This is to consider that the CNR is apt to be reduced as the tube voltage becomes smaller as indicated by the solid line graph of FIG. 16. For instance, when the tube voltage is b (<standard tube voltage xv_ref) and the normalized CNR is c(b), the mAs correction coefficient λ(b) and mAs_corr(b), being the mAs value after the correction, are calculated by the following formula 9 (tube current time product correction means):

$$mAs\_corr(b)=\lambda(b) \times mAs(z\_MAXSD2) \quad \text{(Formula 9)}$$

Here, $\lambda(b)=1/c(b)^2$

It is desirable that the data used for generating the relational chart between the tube voltage and the normalized CNR is obtained by imaging water phantoms having various sizes in the X-ray CT apparatus to be employed. However, data generated on the basis of simulation data may be used.

(10) Calculate Optimum Tube Voltage, Exposure Dose, and X-Ray Tube Power, Under the Condition of Corrected mAs (Step S310)

Basic data of the exposure dose and the X-ray tube power calculated from various conditions in the X-ray CT apparatus to be used or simulation is stored in the storage device 24 in advance. Then, exposure dose (e.g., CTDIw) and X-ray tube power at the slice position of z_MAXSD2 are calculated using the corrected tube current time product mAs_corr for each tube voltage calculated in step S309. The relationship among the tube voltage, exposure dose, and X-ray tube power on this occasion are as shown in FIG. 17. An optimum value of the tube voltage, kV_opt, is the optimum tube voltage that minimizes the exposure dose under the condition where the X-ray tube power kW becomes kW≦kW_max (rated X-ray tube power) (tube voltage calculating means).

In FIG. 17, on the basis of the exposure dose for each phantom size and tube voltage, which is calculated by the X-ray CT apparatus to be employed or the simulation (since the unit is mGy/mAs, the exposure dose is obtained once mAs is calculated), the corrected tube current mAs_corr calculated according to the imaging condition for each tube voltage, is multiplied by the mAs value, so as to generate the relationship between the tube voltage and the exposure dose. Further, the X-ray tube power can be calculated for each tube voltage, according to the calculation; tube voltage×tube current. By utilizing the values above, the relationship between the tube voltage and the X-ray tube power can be generated.

The X-ray tube power is calculated because it is necessary to check whether the X-ray condition being calculated is within the usage range of the X-ray CT apparatus, and to know how long will be a waiting time until an image is taken under this imaging condition. The exposure dose (e.g., CTDIw) is measured pursuant to a global standard of the measurement method CTDIw recommended by the IEC. It is obtained by "converting an average of mAs values that fluctuate within the scan range, into CTDIw as energy absorbed by radiation per unit mass".

(11) Calculate mAs Value Satisfying CNR_det on Other Slice Plane z, and Display Imaging Information such as Image SD, a Recommended Tube Voltage, and Exposure Dose (Step S311)

Under the condition of optimum tube voltage kV_opt obtained in step S310, mAs(z) being mAs value satisfying CNR_det on other slice plane z is calculated according to the formula 9 from the tube voltage-normalized CNR curve as shown in FIG. 16 for each size of photographic object size L (z), and the exposure dose (e.g., CTDIw) and the X-ray tube power under the condition of xv_opt and mAs(z) are calculated.

Then, the display device 5 displays the imaging information, being obtained according to the steps above, such as the assumed contrast value of the diagnostic object, the contrast to noise ratio, the image SD, the identifiable size d_o of the diagnostic object, the exposure dose (CTDIw), the optimum tube voltage, the average tube current (a value obtained by dividing the mAs value by the scan time), and the X-ray tube power (kW). One example of these displayed elements is shown in FIG. 18. Also in this example, the recommended imaging condition that is optimized by the steps above, and the imaging condition without any optimization are displayed for the operator.

As thus described, the recommended imaging condition being optimized and the condition following a conventional imaging condition without optimization are displayed side by side. Therefore, it is possible to clearly present a different point of the recommended X-ray condition optimized by the present embodiment.

According to the procedure above, it is possible to decide an imaging condition that is capable of achieving a CNR appropriate for identifying the diagnostic object. The imaging condition decided as described is stored in the storage device 24. Then, while the system controller 19 calls the condition sequentially in association with an imaging part of the object 17 upon scanning, the X-ray controller 7 carries out scanning by using the tube current obtained by dividing the mAs value by the scan time, according to the mAs value calculated in association with each slice position.

THIRD EMBODIMENT

FIG. 19 is an operational flowchart showing a series of preparatory operations which are performed prior to scanning for deciding an optimum X-ray condition in the third embodiment. Hereinafter, the steps for deciding the X-ray condition will be explained in detail with reference to this operational flowchart. In the present embodiment, an operator sets a target SD as an objective and calculates an identifiable diagnostic object size from the relationship between the diagnostic object size and a CNR, and it is different from the second embodiment in which the CNR is obtained from the relationship between the diagnostic object size and the CNR, and an SD at the reference slice position is obtained from the CNR. The present embodiment has an advantage that an imaging condition based on the CNR can be set according to a method similar to the conventionally used method in which the image SD is inputted to set the imaging condition.

(1) Since the steps of imaging scanogram (S400), setting of scan area, inputting of imaging condition (S401), analysis of scanogram data (S402), up to the generation of three-dimensional model of the object (S403) are the same as the processing from step S300 to step S303 of the second embodiment, explanations of each step will not be made tediously.

(2) Calculate slice position z_MAXSD3 that maximizes the image SD under an identical imaging condition in 3D model (step S404)

A slice position z_MAXSD3 is calculated, which maximizes the image SD under the identical imaging condition within the scan range, from the three-dimensional model of the object 17 that is generated in step S403 (slice position calculating means). This z_MAXSD3 is calculated by analyzing the projection height of the scanogram (the projection height is associated with X-ray attenuation for each slice; the larger is the projection height, the larger is X-ray attenuation, and accordingly the image SD becomes larger). This is the same as the second embodiment.

(3) Input Target Image SD Value SD_dem (Step S405)

SD_dem (target image SD) being an image SD demanded by the operator is inputted and set via the input means of the operating device 6 (target image SD setting means). When a real scan is carried out, the X-ray dose is controlled by the X-ray controller 7, in such a manner that SD_dem is achieved at all the slice positions based on the SD_dem being inputted.

(4) Calculate Identifiable Diagnostic Object Size d from an Assumed Contrast Value at z_MAXSD3 (Step S406)

In this step, a CNR enabling identification is calculated from the assumed contrast value considering the imaging part, the object size, and the like, and the SD_dem inputted in step S405, and a size d of the object identifiable in the diagnosis is inversely calculated according to the concept of formula 2, which represents the relationship between the CNR enabling identification and the diagnostic object size (diagnostic object size calculating means). Then, the size is displayed on the display device 5. The assumed contrast value is the same as the one explained in step S307 of the second embodiment, and it is stored in the storage device 24 in advance in association with a diagnostic object portion, an imaging part, an object physical frame, and the like.

The size d of the object to be displayed can be calculated at the slice position z_MAXSD3 as a reference, which maximizes the image SD under the identical imaging condition, for instance. When the assumed contrast value at z_MAXSD3 is assumed as C_z_MAXSD3, according to the definition of CNR and the formula 2, the following formula 10 is established (assumed contrast value calculating means):

$$\frac{C\_z\_MAXSD3}{SD\_dem} = \qquad \text{[Formula 10]}$$
$$a*d^{-b} \Leftrightarrow d = \left(\frac{a}{C\_z\_MAXSD3}\right)^{\frac{1}{b}} * SD\_dem^{\frac{1}{b}}$$

FIG. 20 schematically illustrates the formula 10. In FIG. 20, SD_ent represents an image SD value entered by the operator, and SD_dem represents the value actually entered. It is possible for the operator to input the SD_dem visually by using a mouse or the like, on the graph of FIG. 20 displayed on the display device 5.

In the case above, since the relationship between the diagnostic object size and the image SD is clarified, it is possible to set the SD_dem more easily. Values stored in advance in the storage device 24 for each imaging part or each diagnostic object may be used as defaults of the assumed contrast value and the SD_dem. Alternatively, the operator himself or herself may input the values via the input unit of the operating device 6. The assumed contrast value inputted is reflected on the formula 10.

(5) Determine Appropriateness of Identifiable Diagnostic Object Size d Being Calculated (Step S407)

In this step, the operator determines whether or not the identifiable size d (diameter r of a circle having an area equal to the diagnostic object) displayed in step S406 is appropriate, for a portion of diagnosis or a degree of disease (diagnostic object size determination means). If it is determined as appropriate, the next step is S408, whereas if it is determined as not appropriate, the process goes again to steps S405 and S406, while the operator adjusts the image SD (image SD value adjusting means). The procedure from the step S408 is the same as the second embodiment, except that the SD used as a standard is SD_dem, which is the target SD value.

(6) Calculate mAs(SD_dem) Satisfying the SD_dem at z_MAXSD3 when the Object Size is L (Step S408)

In this step, mAs(SD_dem) is calculated, which is a tube current time product satisfying the SD_dem on the image SD-tube current time product mAs curve as shown in FIG. 15, when the object size is L at the slice position z_MAXSD3 (tube current time product calculating means). The tube voltage condition in this case is the standard tube voltage xv_ref.

(7) Calculate mAs Correction Coefficient and Correct mAs for Keeping the CNR Constant Irrespective of Tube Voltage, on the Basis of the Relationship Between the Tube Voltage and CNR, when the Object Size is L Under the Condition of mAs(SD_dem) (Step S409)

According to the tube voltage-normalized CNR curve as shown in FIG. 16 under the condition that the object size L and mAs(SD_dem), an mAs correction coefficient is calculated for keeping the CNR constant irrespective of the tube voltage (tube current time product correction coefficient calculating means). More particularly, under the condition of mAs (SD_dem) calculated in step S408, on the basis of the tube voltage-normalized CNR curve when the object size is L, mAs correction coefficient $\lambda$ is calculated by the formula 9 for keeping the CNR approximately constant, irrespective of the tube voltage.

Then, the mAs(SD_dem) is corrected by the mAs correction coefficient, and a corrected mAs is obtained (tube current time product correction means)

(8) Calculate Optimum Tube Voltage, Exposure Dose, and X-Ray Tube Power, Under the Condition of the Corrected mAs (Step S410)

The exposure dose (e.g., CTDIw) and X-ray tube power at the slice position of z_MAXSD3 are calculated, using the corrected mAs calculated for each tube voltage in step S409. The calculation method is the same as step S310 of the second embodiment. The optimum value kV_opt of the tube voltage is to minimize the exposure dose under the condition where the X-ray tube power kW$\leq$kW_max (tube voltage calculating means).

(9) Calculate mAs Value Satisfying the SD_dem on Other Slice Plane z, and Display Image SD, Recommended Tube Voltage, Exposure Dose, and the Like (Step S411)

Under the condition of the optimum tube voltage kV_opt obtained in step S410, mAs(z) being the mAs value satisfying the SD_dem at other slice plane z is calculated by the formula 9 from the tube voltage-normalized CNR curve for each object size L(z) as shown in FIG. 16, and the exposure dose (e.g., CTDIw) and X-ray tube power under the condition of kV_opt and mAs(z) are calculated.

The imaging condition information obtained according to the procedure above, such as the assumed contrast value of the diagnostic object, the contrast to noise ratio, the image SD, the identifiable size d of the diagnostic object, the exposure dose (CTDIw) and the X-ray tube power (kW), is displayed on the display device 5. Also in this displaying process, similar to the display example of the second embodiment (FIG. 18), the recommended imaging condition being optimized by the present embodiment and the condition following a conventional imaging condition without optimization are shown side by side for the operator. Therefore, it is possible to clearly present a different point of the recommended X-ray condition optimized by the present embodiment.

As thus described, according to the third embodiment, it is possible to decide an imaging condition that allows an acquisition of a CNR appropriate for identifying the diagnostic object. Furthermore, some operators who are accustomed to a system for inputting an image SD, such as automatic exposure mechanism conventionally used, are allowed to decide easily an imaging condition with little inhibitions in applying the present embodiment. The thus decided imaging condition is stored in the storage device 24. Then, while the system controller 19 calls the condition sequentially in association with an imaging part of the object 17 upon scanning, the X-ray controller 7 carries out scanning by using the tube current obtained by dividing the mAs value by the scan time, according to the mAs value calculated in association with each slice position.

FOURTH EMBODIMENT

FIG. 21 is an operational flowchart showing a series of preparatory operations which are performed prior to scanning for deciding an optimum X-ray condition in the fourth embodiment. Hereinafter, the steps for deciding the X-ray condition will be explained in detail with reference to this operational flow. From the first to the third embodiments, the tube voltage and tube current (or the tube current time product) are calculated initially at the slice position (the reference slice position) where the SD value is maximized within the particular slice range. On the other hand, the present embodiment is different from the above embodiments in the point that the slice position that maximizes the SD value is not used as a reference, but an operator designates a desired slice position. Therefore, in the present embodiment, the processing varies depending on whether or not the calculated CNR is applicable to all the slices.

(1) Since the steps of imaging scanogram (S500), setting of scan area, inputting of imaging condition (S501), analysis of scanogram data (S502), up to the generation of three-dimensional model of the object (S503) are the same as the processing from step S300 to step S303 of the second embodiment, and as the processing from step S400 to step S403 of the third embodiment, explanations of each step will not be made tediously.

(2) Designate Slice Position z_def (Step S504) and Input FPF and Diagnostic Object Size d_o (Step S505)

In these steps, an operator designates a desired slice position z_def (desired slice position designating means), and inputs and sets the FPF and the diagnostic object size d_o (false positive fraction setting means and diagnostic object size setting means). The slice position may be designated by specifying a slice section or a volume.

(3) Calculate CNR_d which Enables Identification of the Diagnostic Object from the Assumed Contrast Value and the Image SD (z_def) at the Desired Slice Position z_def (Step S506)

With the assumed contrast value considering the imaging part, the object size, and the like, and the desired slice position z_def designated in step S504, an image SD value SD(z_def) at the desired slice position z_def are obtained from the object 3D model calculated in step S503 by using the image SD predictive function (desired slice position image SD predicting means).

The data obtained by imaging water phantoms of various sizes in the X-ray CT apparatus to be employed and analyzing the image SD, or data generated based on simulation data, is used for predicting SD(z_def). These data items are stored in the storage device 24. A three-dimensional model of the object is established at the slice position z_def and is compared to the data stored in the storage device 24 so that the image SD is predicted.

Using the image SD(z_def) predicted according to the above procedure, the contrast to noise ratio enabling identification CNR_d within the diagnostic object area at the slice position z_def can be calculated according to the following formula 11 (third contrast to noise ratio calculating means):

$$CNR\_d = \text{assumed contrast value}/SD(z\_def) \quad \text{(Formula 11)}$$

(4) Determine Whether or Not the Image SD(z_def) at the Desired Slice Position z_def is within the Marginal Performance Range of the Device (Step S507)

In this step, it is determined whether or not the image SD(z_def) in the three-dimensional model of the object calculated in step S506 is feasible in the X-ray CT apparatus being employed (image SD predictive value feasibility determination means).

For the determination, the relationship between the image SD and the tube current time product mAs as shown in FIG. 15 is used under the condition of the three-dimensional model of the object being calculated. Software refers to a configuration file of the X-ray CT apparatus regarding the mAs that satisfies SD(z_def), thereby determining whether or not the mAs is within the marginal performance range of the X-ray CT apparatus. It is to be noted that the configuration file is a parameter setting file in which a combination of various imaging conditions, operational conditions as CT system, and the like, are described.

In making the determination above, if it is determined as feasible in the X-ray CT apparatus, the next step is S508, whereas if it is determined as unfeasible, the procedures from step S505 to S507 are repeated, while the operator changes the parameters (false positive fraction and diagnostic object size adjusting means).

(5) Determine Whether or Not CNR_d is Applicable to All the Slice Positions (Step S508)

It is further determined whether or not the CNR_d calculated in step S506 is applicable to all over the scan area set in step S501 (contrast to noise ratio determination means). If it is applicable to all the slice positions, the next step is S509, whereas if it is not applicable, the next step is S510.

(6) Calculate mAs Correction Coefficient, Calculate Optimum Tube Voltage kV_opt and Corrected mAs, and Display the Imaging Condition (Step S509)

This step is the same as steps S308 to S311 in the second embodiment. It is to be noted, however, that the descriptions z_MAXSD2 and SD(z_MAXSD2) in the second embodiment are replaced by z_def and SD(z_def), respectively (tube current time product calculating means, tube current time product correction coefficient calculating means, tube current time product correction means, and tube voltage calculating means).

Here, as to some of the object sizes (diameter r) in association with the slice positions, the mAs value may exceed the marginal performance range of the X-ray CT apparatus in order to achieve the CNR_d. In this case, modification is made to achieve a CNR which is close to the CNR_d as possible, and scanning is performed using a limit value within the performance range which is acceptable to the device. In the case above, as shown in FIG. 22 with the mark of "o", it is possible to clearly demonstrate the operator the slice position that is not able to achieve the CNR_d, by a highlighting on the display device 5. It is further possible not to demand the marginal performance of the device in the area other than the focused slice position designated by the operator, as indicating "Apply device marginal output" in FIG. 22.

In the present embodiment, radio buttons are provided to indicate locations corresponding to the slice positions, respectively, so as to establish a configuration to place a checkmark for the slice position where imaging with critical power output is performed. Instead, there is another implementing method such as clicking the slice position by a mouse, and the method for implementation is not limited to the example as described above.

By employing the method described above, the operator is allowed to check in advance a position where the CNR_d is not guaranteed on the image being displayed. In addition, by setting that the marginal performance of the device is not demanded depending on the slice position, unnecessary exposure is suppressed, enabling a further reduction of exposure dose.

(7) Determine Whether or Not SD(z_def) is Applicable to All the Slice Positions (Step S510)

If it is determined in step S508 that the CNR_d calculated in step S506 is not applicable to the whole scan area, this step further determines whether or not the SD(z_def) is satisfactory at all the slice positions, according to the examination details and the diagnostic area (all slice positions applicability determination means).

If it is determined that the SD(z_ref) is satisfactory at all the slice positions in step S510 (all slice positions applicability determination means), the next step is S511. If it is determined that the SD(z_ref) is not applicable to all the slice positions, the next step is S514.

(8) Calculate mAs(z) Satisfying SD_def (Step S511)

The imaging condition is controlled so that the image SD_def is satisfied irrespective of the slice position, and with reference to FIG. 15, mAs(z) that achieves the SD_def is calculated by using the image SD predictive function for each object size L(z) (the second tube current time product calculating means). Since FIG. 15 is a curve of the image SD-tube current time product mAs of the object size L at z_MAXSD2, mAs(z) can be calculated from the curve for each object size L(z) in association with the slice position z. Since the method keeps the image SD equivalent to that of the designated slice position, it is effective in generating an image by MPR (multi-planar reconstruction), or the like.

(9) Calculate Exposure Dose and X-Ray Tube Power Under the Condition of mAs(z) that Satisfies SD_def for Each Slice Position at the Optimum Tube Voltage xv_opt (Step S512)

In this step, the diagnostic object size L(z) of the object and the object size L(z_def) at the slice position z_def being designated are compared (object size comparing means), and the following process is performed.

Firstly, for the case of $L(z) \leq L(z\_def)$, the processing similar to step S509 is performed (the third tube current time product calculating means, tube current time product correction coefficient calculating means, tube current time product correction means, and tube voltage calculating means).

For the case of L(z)>L(z_def), by using the optimum tube voltage kV_opt calculated in the case where L(z)≦L(z_def), the exposure dose (e.g., CTDIw) and the X-ray tube power under the condition of mAs(z) are calculated for each slice position z. As for the mAs(z) in the case where L(z)>L(z_def), an mAs value satisfying the SD_def is calculated from the image SD-tube current time product mAs curve as shown in FIG. 15 at the optimum tube voltage xv_opt. Then, a coefficient for correcting the calculated mAs value is obtained in the same manner as the case where L(z)≦L(z_def), and then the mAs value is corrected. The optimum value of the tube voltage on this occasion is an optimum tube voltage that minimizes the exposure dose under the condition that the X-ray tube power kW satisfies kW≦kW_ref (a reference value of the X-ray tube power) (tube power calculating means).

There may be a slice position where the mAs value satisfying the image SD_def goes over the marginal performance of the X-ray CT apparatus, depending on the diagnostic object size L(z) of the object. In this case, the imaging parameter is adjusted so as to approach the SD_def as close as possible, and scanning is performed with the marginal performance of the X-ray CT apparatus. Then, for the operator, it is also possible to clearly demonstrate the slice position which is not able to achieve the SD_def, by highlighting on the display device 5, as shown in FIG. 22. It is further possible not to demand the marginal performance of the device in the area other than the focused slice position designated by the operator.

Also in the present embodiment, radio buttons are provided to indicate locations corresponding to the slice positions, respectively, so as to establish a configuration to place a checkmark for the slice position where imaging with critical power output is performed. Instead, there is another implementing method such as clicking the slice position by a mouse, and the method for implementation is not limited to the example as described above.

By employing the method described above, the operator is allowed to check in advance a position where the SD_def is not guaranteed on the image being displayed. In addition, since the settings are configured so that the marginal performance of the X-ray CT device is not demanded depending on the slice position, unnecessary exposure is suppressed, enabling a further reduction of exposure dose.

(10) Display Information such as Image SD, Identifiable Size of Diagnostic Object, Exposure Dose, X-Ray Tube Power (Step S513)

The information decided in step S512, such as the tube voltage, the tube current (average tube current obtained by dividing mAs by the scan time), the image SD, the identifiable size of the diagnostic object, the exposure dose, the X-ray tube power, and the like, is displayed on the display device 5, and then imaging is started.

(11) Calculate mAs(z_def) Satisfying SD(z_def) at z_def by Using the Image SD Predictive Function (Step S514)

In step S510, if it is determined that the SD(z_def) is not applied to all the slices, imaging is carried out at all the slice positions with the tube current time product mAs(z_def) which satisfies CNR_d at the slice position z_def. Here, the mAs(z_def) is calculated by using the image SD predictive function at the object size L(z_def) (the fourth tube current time product calculating means). Since an identical mAs can be used at all the slice positions in this method, there is an advantage that drastically simplifies the tube current control.

(12) Calculate Exposure Dose and X-Ray Tube Power for Each Slice Position Under the Condition of mAs(z_def), with Respect to All the Tube Voltages Being Available (Step S515)

By using the tube current time product mAs (z_def) calculated in step S514, the exposure dose (e.g., CTDIw) and X-ray tube power at the slice position z_def are calculated with respect to all the available tube voltages (exposure dose and X-ray tube power at designated slice position calculating means). On this occasion, the optimum value kV_opt of the tube voltage is the tube voltage that minimizes the exposure dose under the condition that X-ray tube power kW satisfies kW≦kW_max (tube voltage calculating means).

(13) Display Information such as Image SD, Identifiable Size of Diagnostic Object, Exposure Dose, X-Ray Tube Power (Step S516)

The information decided in step S515, such as the tube voltage, the tube current (average tube current obtained by dividing mAs by the scan time), the image SD, the identifiable size of the diagnostic object, the exposure dose, the X-ray tube power, is displayed on the display device 5, and then imaging is started.

In the description explained so far, it is determined whether or not SD(z_def) is satisfactory at all the slice positions according to the examination details and the diagnostic area, when the operation moves to step S511 and to step S514. However, it is further possible to perform the procedure from the step S511 and S514 without going through the step S510, and after displaying the information such as the image SD, the identifiable size of the diagnostic object, the exposure dose, and the X-ray tube power, being decided in step 513 and step S516, the operator may select an imaging condition that the operator considers as the most suitable for the examination.

As thus described, according to the fourth embodiment, the operator designates a desired diagnostic area, and thereby the imaging condition that allows an acquisition of a CNR appropriate for identifying the diagnostic object can be decided. Accordingly, it is possible to reduce the exposure dose to the degree approximately the same as the third embodiment.

The imaging condition decided as thus described is stored in the storage device 24. Then, while the system controller 19 calls the condition sequentially in association with an imaging part of the object 17 upon scanning, the X-ray controller 7 carries out scanning by using the tube current obtained by dividing the mAs value by the scan time, according to the mAs value calculated in association with each slice position.

FIFTH EMBODIMENT

FIG. 23 is an operational flowchart showing a series of preparatory operations which are performed prior to scanning for deciding an optimum X-ray condition in the fifth embodiment. Hereinafter, the steps for deciding the X-ray condition will be explained in detail with reference to this operational flowchart. The present embodiment allows setting of multiple regions of interest and a recommended imaging condition is calculated for each region of interest. The present embodiment is almost the same as the second embodiment other than the point above.

(1) Since the steps of imaging scanogram (S600), setting of real scan area, inputting of imaging condition (S601), analysis of scanogram data (S602), up to the generation of three-dimensional model of object (S603) are the same as the processing from step S300 to step S303 of the second embodiment, the processing from step S400 to step S403 of the third embodiment, and from step S500 to step S503 of the fourth embodiment, explanations of each step will not be made tediously.

(2) Set Multiple Regions of Interest (Step S604)

Multiple regions of interest are set within the real scan area provided in step S601, as to which the operator desires to change the conditions respectively (multiple regions of interest setting means). In the following explanations, each number of the multiple regions being set is assumed as n.

(3) Input FPF(n) and Diagnostic Object Size d_o for Each Region (Step S605)

An operator inputs FPF(n) as a guide used for a diagnosis and a size of the diagnostic object (e.g., contrast-enhanced liver cell cancer) d_o for each region being set (diagnostic object size setting means and multiple false positive fraction setting means). The diagnostic object size d_o is assumed as a diameter r of a circle having an area equivalent to the diagnostic object (circle equivalent diameter), for instance.

FIG. 24 is a schematic illustration showing the case where there are two regions of interest. For example, the lung field area is set as the region of interest 1 (Region of Interest 1: ROI 1), and the lever field is set as the region of interest 2 (Region of Interest 2: ROI 2). Then, the diagnostic object sizes of the regions are assumed as d_o(1) and d_o(2), respectively.

(4) Calculate CNR_d(n) which can Identify the Diagnostic Object in Each Region of Interest Being Set (Step 606)

CNR_d (n) to be achieved is calculated on the basis of the diagnostic object size that the operator inputted in step S605 (the fourth contrast to noise ratio calculating means). Similar to the second embodiment, the relationship between the CNR enabling identification and the diagnostic object size, the relational diagram between the FPF and the TPF, and the relational diagram between the CNR enabling identification and the FPF, as shown in FIG. 12 and FIG. 13, are used for calculating the CNR which is to be achieved. The CNR enabling identification is corrected based on the slice thickness and the window condition, similar to the first embodiment.

(5) Calculate Slice Position z_ref(n) that Maximizes the Image SD for Each Region of Interest, being Set in the 3D Model of the Object (Step S607)

A slice position z_ref(n) is calculated, which maximizes the image SD under the identical imaging condition for each region of interest (ROI) set in step S604, from the object three-dimensional model generated in step S603 (slice position calculating means).

(6) Calculate Image SD(z_ref(n)) at the Slice Position z_ref (n), Based on the Assumed Contrast Value and CNR_d(n) (Step S608)

In this step, according to the assumed contrast value considering the imaging part, the object size, and the like, and the CNR_d(n) calculated in step S606, the image SD(z_ref(n)) at the slice position z_ref(n) obtained in step S607 is calculated (image SD value calculating means).

(7) Calculate mAs(z_ref(n)) Satisfying the SD(z_ref(n)) at the Slice Position z_ref(n) when the Object Size is L(z_ref (n)) (step S609)

In this step, mAs(z_ref(n)) satisfying the SD(z_ref(n)) at the position z_ref(n) when the object size is L(z_ref(n)) is calculated on the image SD-tube current time product mAs curve as shown in FIG. 15 (tube current time product calculating means). The tube voltage condition of the image SD-tube current time product mAs curve is assumed, for instance, as 120 kV (hereinafter, it is referred to as standard tube voltage xv_ref).

(8) Calculate mAs Correction Coefficient and Correct mAs for Keeping CNR to be Approximately Constant Irrespective of the Tube Voltage, Under the Condition of the Object Size L (z_ref(n)) and mAs (z_ref(n)) (Step S610)

Under the condition of mAs (z_ref(n)) calculated in step S609, an mAs correction coefficient is calculated for keeping the CNR to be approximately constant irrespective of the tube voltage, based on the tube voltage-normalized CNR curve as shown in FIG. 16 when the object size is L(z_ref(n)) (tube current time product correction coefficient calculating means). The calculation method of the mAs correction coefficient is the same as the second embodiment.

By using the mAs correction coefficient, the mAs(z_ref(n)) being calculated above is corrected according to the formula 9 (tube current time product correction means). Hereinafter, the corrected mAs is described as mAs_corr(n).

(9) Calculate Exposure Dose and X-Ray Tube Power at the Slice Position z_ref(n) when the Tube Current Time Product is mAs_corr(n) (step S611)

The exposure dose (e.g., CTDIw) and X-ray tube power at the slice position z_ref(n) are calculated for each tube voltage calculated in step S610 after the tube current time product is corrected as mAs_corr(n). Data of the exposure dose is stored in advance in the storage device 24, and kV_opt(n) being the optimum value of the tube voltage is the voltage that minimizes the exposure dose, under the condition that the X-ray tube power kW satisfies $kW \leq kW\_max(n)$ (tube voltage calculating means).

(10) Calculate mAs Satisfying SD(z_ref(n)) on Other Slice Plane by Using the Optimum Tube Voltage kV_opt(n) and Display Information, such as the Image SD, the Identifiable Size of the Diagnostic Object, the Exposure Dose, and the X-Ray Tube Power (Step S612)

Under the condition of the optimum tube voltage xv_opt(n) selected in step S611, an mAs value satisfying the SD(z_ref (n)) on other slice plane is calculated by the image SD predictive function. The mAs_corr(z(n)) is calculated from the tube voltage-normalized CNR curve for each slice plane with the calculated mAs, and the exposure dose (e.g., CTDIw) and X-ray tube power are calculated under the imaging condition selected in step S611. The mAs value being calculated as described above is used for the tube current control in the X-ray controller 7.

Thereafter, the information such as the assumed contrast value of the diagnostic object, the contrast to noise ratio, the optimum tube voltage, the average tube current, the image SD, the identifiable size of the diagnostic object, the exposure dose, and the X-ray tube power, is displayed on the display device. An example of displaying these items is the same as the example shown in FIG. 18, for instance.

In the fifth embodiment, if more than one diagnostic area is set, the image SD is different for each imaging region. Therefore, when a three-dimensional image is reconstructed, a slice plane may exist where a drastic change occurs in the image SD. Accordingly, it is desirable to employ a system that controls the imaging rays to make the variation of the image SD smooth on the slice planes, before and after the image SD changes drastically.

According to the procedure described above, it is possible to decide an imaging condition that is able to achieve the CNR appropriate for identifying the diagnostic object. It is anticipated that a lesion as a target of the diagnosis may be obviously different area by area, and an appropriate condition can be set for each imaging region. Accordingly, it is possible to reduce unnecessary exposure. The imaging condition being decided is stored in the storage device 24, and the system controller 19 sequentially calls the condition in association with the imaging part of the object 17 upon scanning, thereby controlling the X-ray dose.

It is to be noted here that also in the four preferable embodiments from the second to the fifth, similar to the first embodiment, a selection means can be provided (X-ray condition selection means) for selecting an arbitrary imaging condition from the recommended imaging condition and other imaging conditions. According to this selection means, a radiologist is allowed to select the imaging condition depending on the usage purpose, and this configuration renders the system more flexible.

The imaging condition as decided above is stored in the storage device 24 and the system controller 19 sequentially reads out the imaging condition in association with the imaging part of the object 17 when scanning is done, so as to control the imaging condition (tube voltage and tube current) during the scan via the X-ray controller 7.

SIXTH EMBODIMENT

In the second embodiment to the fifth embodiment, there is described a case where both the tube current and the tube voltage are optimized. In the present embodiment, in order to allow the CNR to be a desired value irrespective of the slice position, the tube voltage is not changed from the user set value, but only the tube current is optimized. The present embodiment includes the following advantages:

(1) When the tube voltage is changed to the optimum tube voltage that is different from the user setting value, the X-ray spectrum varies, thereby varying the CT value of each tissue. Since a clinical diagnosis may be conducted by using the CT value of tissue, it is advantageous to prevent such variation of the CT value; and (2) It is sometimes preferable to take images at an identical tube voltage so as not to change the image impression, if a current image and a past image are compared as to an identical patient.

FIG. 25 is an operational flowchart showing a series of preparatory operations which are performed prior to scanning for deciding an optimum X-ray condition in the sixth embodiment. Hereinafter, the steps for deciding the X-ray condition will be explained in detail with reference to this operational flow.

Image Scanogram (Step S700)

A scanogram of the object 17 is imaged. Since taking this scanogram image is the same as step S100 of the first embodiment, detailed explanation will not be made tediously.

Set Scan Area and Input Imaging Condition (Step S701)

This process is the same as the process from step S110, S120, S130, and S140 of the first embodiment. An operator refers to the scanogram image and sets via the operating device 6, an imaging region (scan start position zs and scan end position ze) including the diagnostic object. Here, as the imaging condition of the slice position, a slice thickness, a top panel moving pitch, a scan time, a standard tube voltage, a standard tube current, an X-rays collimation condition, types of reconstruction filter function, an FOV size, a window condition, and the like, are inputted.

Analyze Scanogram Data (Step S702) and Generate Object 3D Model (Step S703)

Similar to the steps S160 and S170 of the first embodiment, the scan planning device 25 analyzes scanogram projection data, and generates an object three-dimensional model of the object 17.

Input Diagnostic Object Size d_o, TPF and FPF (Step S704)

A size of the diagnostic object (e.g., contrast enhanced liver cell cancer) d_o is inputted and set via the input unit of the operating device 6. Furthermore, the operator inputs and sets TPF and FPF being used as a guide for diagnosis via the input unit of the operating device 6 (true positive fraction and false positive fraction setting means). The diagnostic object size is assumed as a diameter r of a circle having an area equivalent to the diagnostic object (circle equivalent diameter), for instance.

Calculate CNR_det that Enables Identification of the Diagnostic Object (Step S705)

CNR_det, which allows the identification of the diagnostic object, is obtained from the diagnostic object size d_o inputted by the operator in step S704 (the second contrast to noise ratio calculating means) The CNR_det enabling identification is calculated similar to the second embodiment, by using the relationship as shown in FIG. 12 and FIG. 13 described in the second embodiment. According to the procedure being the same as the procedure as shown in FIG. 7 described in the first embodiment, the CNR_det enabling identification is obtained, which is corrected based on the slice thickness and window condition.

Calculate Image SD(Z) for Each Slice Plane, the Image SD(z) Satisfying Assumed Contrast Value and CNR_det on the 3D Model Being Generated (Step S706)

In this step, according to the assumed contrast value C_d considering the imaging part, the object size, and the like, and the CNR_det enabling identification calculated in step S705, SD(Z) being the image SD at each slice position is calculated in the same manner as the second embodiment, by using the formula 7 (image SD value calculating means).

The assumed contrast value C_d indicates, when assuming a situation for imaging the liver area, for instance, an absolute value of CT value difference between the liver cell cancer as the diagnostic object and the liver substance. Here, the assumed contrast value at the liver becomes larger in proportion to the density of the contrast agent administered to a patient. In addition, the larger the object size is, the smaller becomes the assumed contrast value. Calculation of the assumed contrast value can be performed by using the formula 8 as described in the second embodiment.

The assumed contrast value is stored in advance in the storage device 24, in association with a diagnostic object portion, an imaging part, an object physical frame, and the like.

Calculate mAs (Z) Satisfying SD(Z) for Each Slice Plane when the Object Size is L(Z) Under the Condition of User Setting Tube Voltage (kV_usrset), and Display the Image SD, Identifiable Size of Diagnostic Object, Exposure Dose, X-Ray Tube Power, and the Like (Step S707)

Calculation of the mAs(Z) can be conducted according to the relationship between the image SD when the object size is L and the tube current time product mAs as shown in FIG. 15. Here, depending on the object size for each slice position, the mAs value for achieving the CNR_d may exceed the marginal performance range of the X-ray CT apparatus. In this case, modification is made to achieve a CNR which is close to the CNR_d as possible, and scanning is performed at a limit value within the marginal performance range of the device. Then, for the operator, it is also possible to clearly demonstrate the slice position which is not able to achieve the CNR_det enabling identification, by highlighting on the display device 5, as shown in FIG. 22. It is further possible not to demand the marginal performance of the device in the area other than the focused slice position designated by the operator.

By employing the method described above, the operator can check in advance a position where the CNR_d is not guaranteed on the image being displayed. In addition, since the settings are configured so that the marginal performance of the device is not demanded depending on the slice position, unnecessary exposure is suppressed, enabling a further reduction of exposure dose.

Then, the imaging condition of the diagnostic object, having been obtained as described above, is displayed on the display device 5, such as the assumed contrast value, the contrast to noise ratio, the image SD, the identifiable size d_o of the diagnostic object, the exposure dose (CTDIw), the tube voltage, the average tube current (a value obtained by dividing mAs value by scan time), and the X-ray tube power (kW). On this occasion, the relationship between the exposure dose and the X-ray tube power is as shown in FIG. 26, and at the slice position where the object size becomes smaller, both the exposure dose and X-ray tube power also become smaller.

As thus described, the recommended imaging condition being optimized by the present embodiment and the condition following a conventional imaging condition without optimization are shown side by side for the operator. Therefore, it is possible to clearly present a different point of the X-ray recommended condition optimized by the present embodiment.

The present embodiment allows a setting of imaging condition enabling an attainment of a CNR appropriate for identifying the diagnostic object, under the tube voltage condition set by a user. The imaging condition determined as thus described is stored in the storage device 24. Then, while the system controller 19 calls the condition sequentially in association with an imaging part of the object 17 upon scanning, the X-ray controller 7 carries out scanning by using the tube current obtained by dividing the mAs value by the scan time, according to the mAs value calculated in association with each slice position.

Similar to the first embodiment, in the other five preferable embodiments from the second to the sixth, the devices such as the system controller 19, the scan planning device 25, and the operating device 6, for executing the aforementioned functions and processing can be implemented by a configuration that operates according to computer programs, the configuration combining a processor, computer, memory, storage device, register, timing control, interruption, communication interface, I/O signal interface, and the like. The present invention is not limited to the examples of the five preferable embodiments from the second to the sixth, and it should be understood the disclosed embodiment is susceptible of changes and modifications without departing from the scope of the invention.

BRIEF DESCRIPTION OF DRAWINGS

FIG. 8 illustrates correction of CNR;

FIG. 9 is a chart showing the relationship between the tube voltage and the image SD;

FIG. 10 illustrates an example of information display regarding the options of X-ray condition;

FIG. 17 is a chart showing the relationship between the tube voltage, and, the exposure dose and the X-ray tube power consumption;

FIG. 18 illustrates an example of information display regarding the X-ray condition;

FIG. 19 is an operational flowchart of preparatory operations prior to scanning by the X-ray CT apparatus to which the third embodiment of the present invention is applied;

DENOTATION OF REFERENCE NUMERALS

Figure 1:
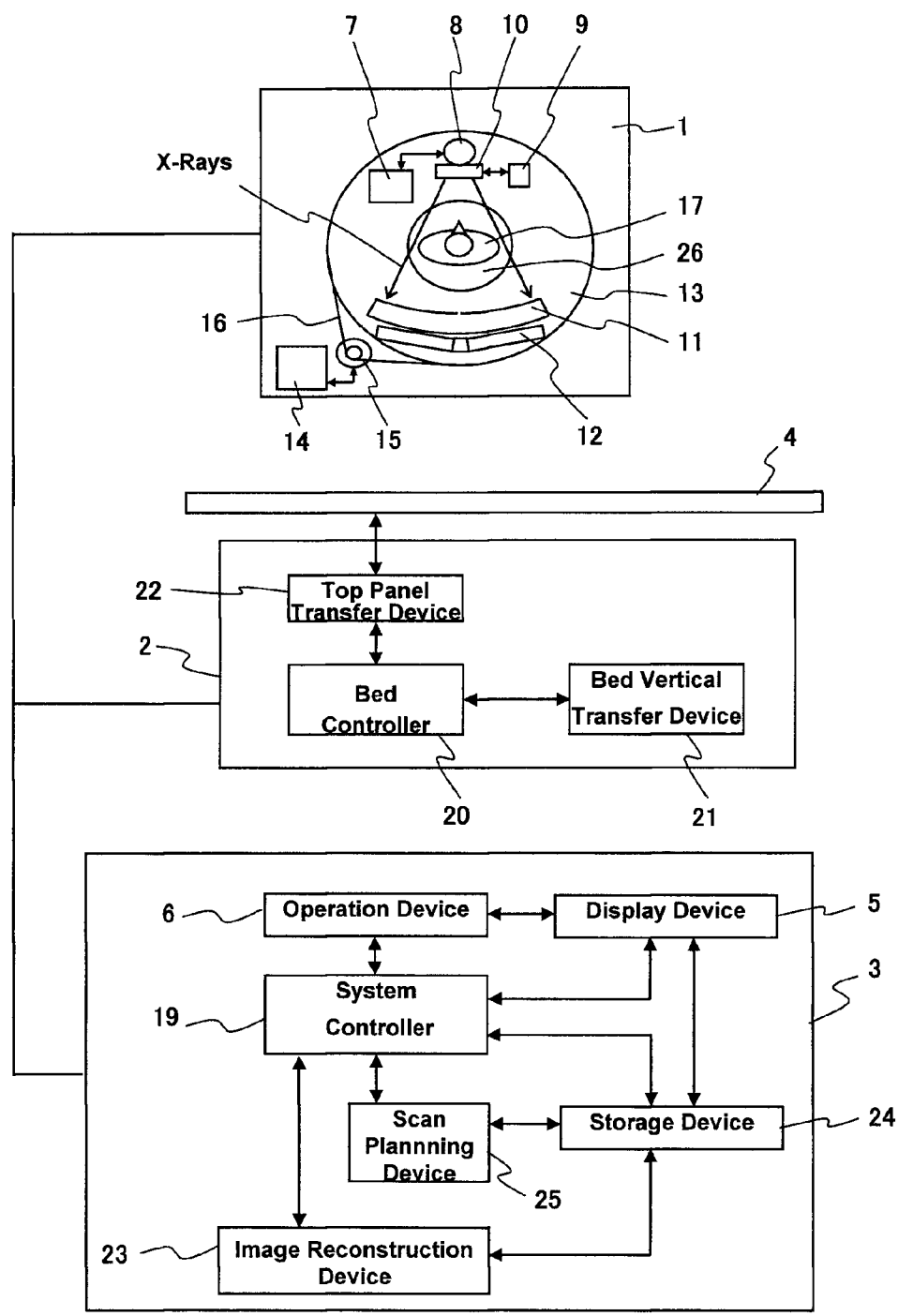
FIG. 1 is an overall configuration diagram of the X-ray CT apparatus to which the present invention is applied.
Figure 2:
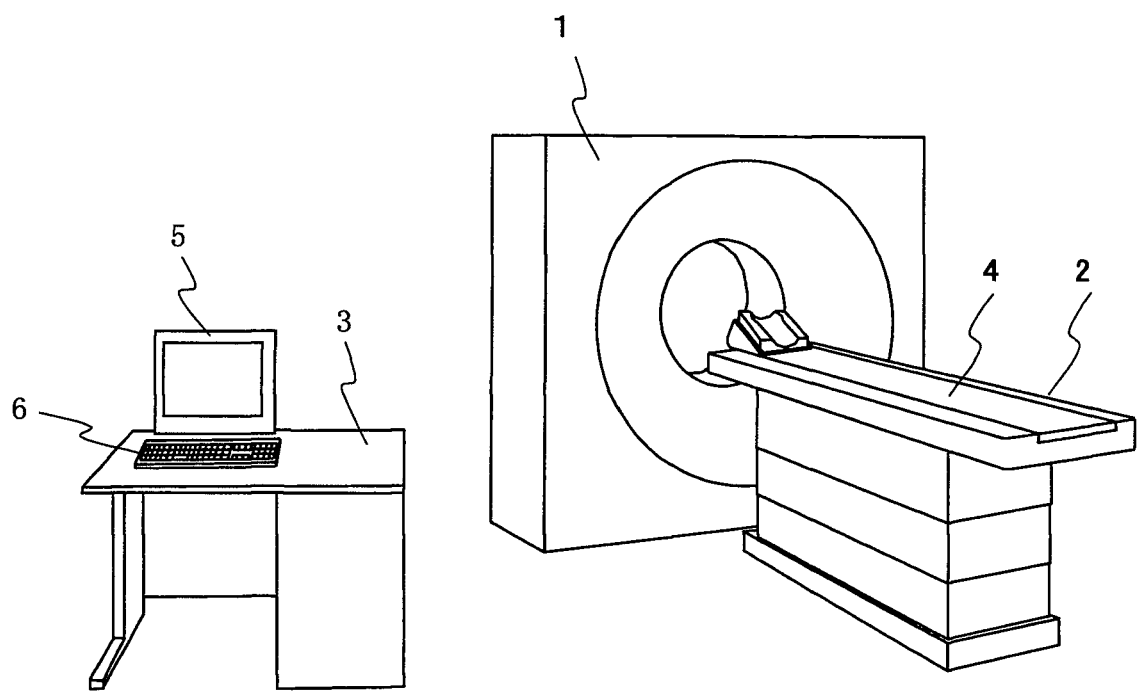
FIG. 2 is an overall schematic view of the X-ray CT apparatus to which the present invention is applied.
Figure 3:
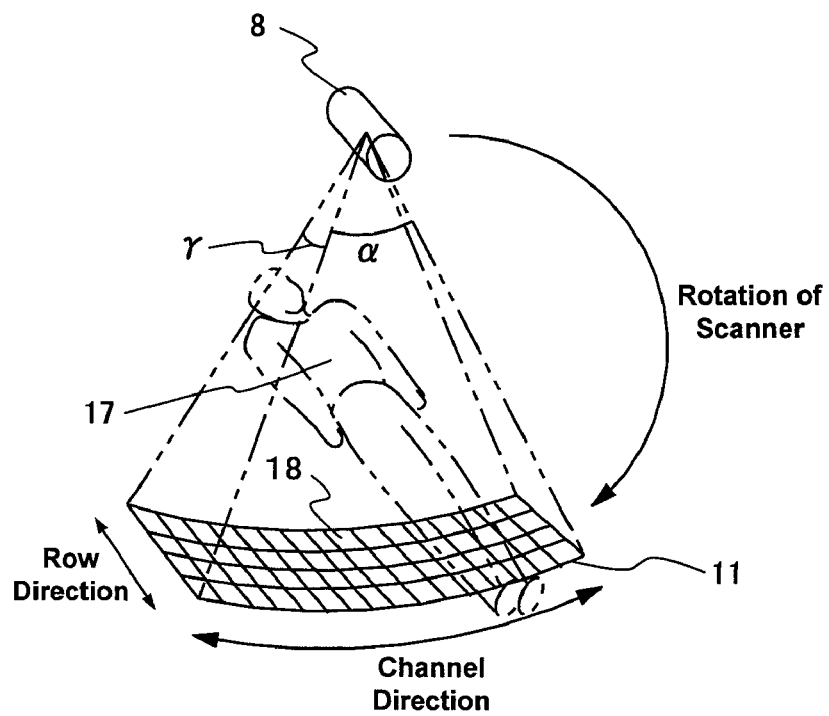
FIG. 3 is a schematic illustration of the configuration of X-ray detector of the X-ray CT apparatus to which the present invention is applied together with its relation to X-ray irradiation.
Figure 4:
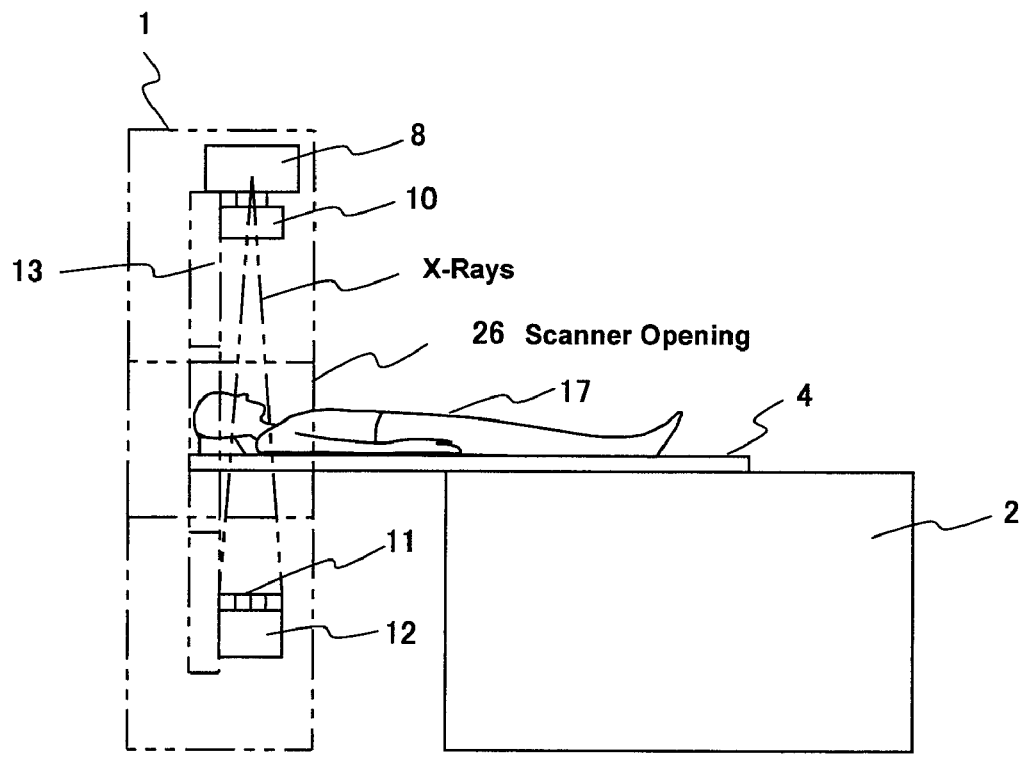
FIG. 4 is a side view showing the relationship among the scanner gantry of the X-ray CT apparatus to which the present invention is applied, the table for patient, and the object.
Figure 5:
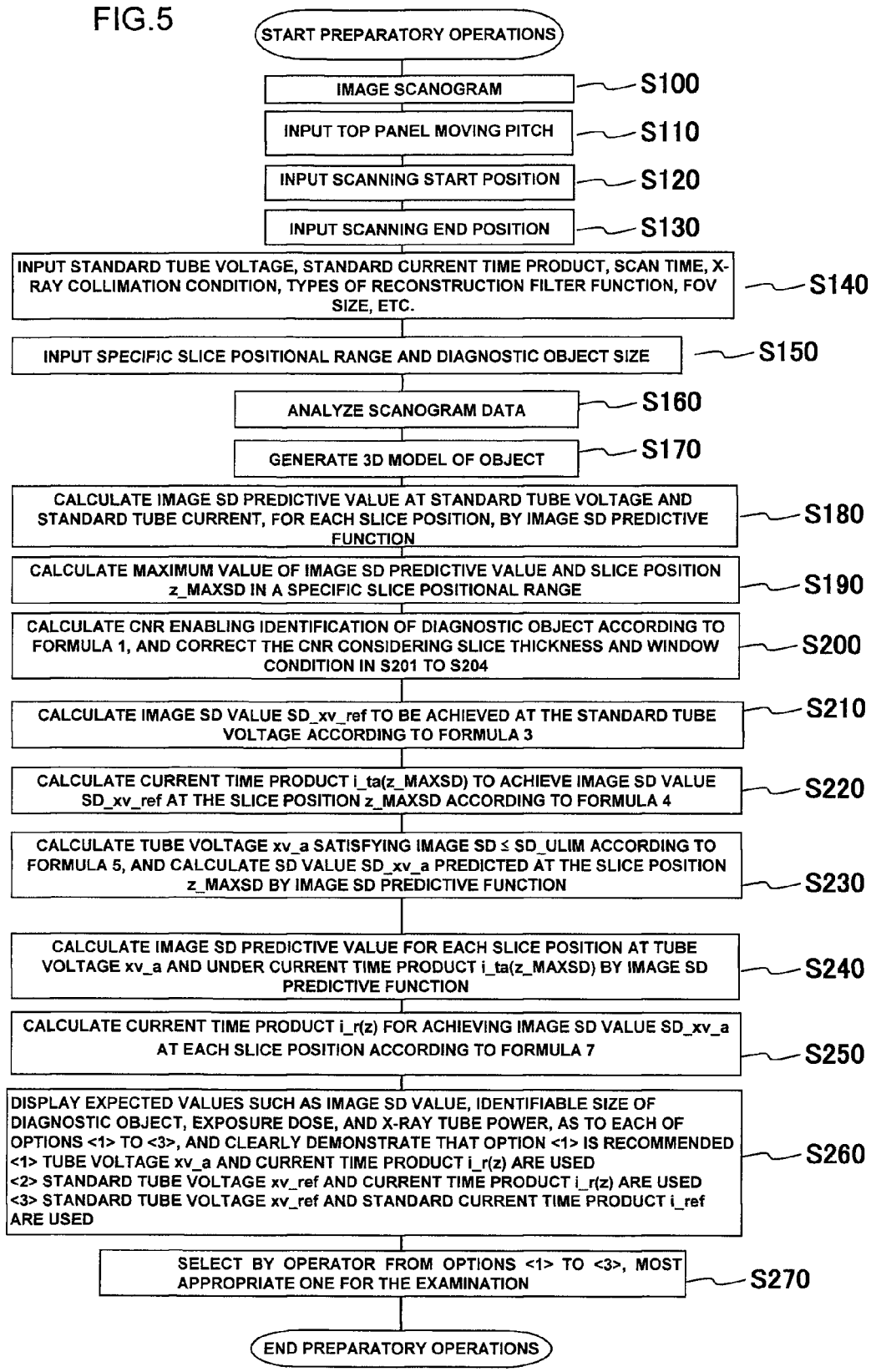
FIG. 5 is an operational flowchart of preparatory operations prior to scanning by the X-ray CT apparatus to which the first embodiment of the present invention is applied.
Figure 6:
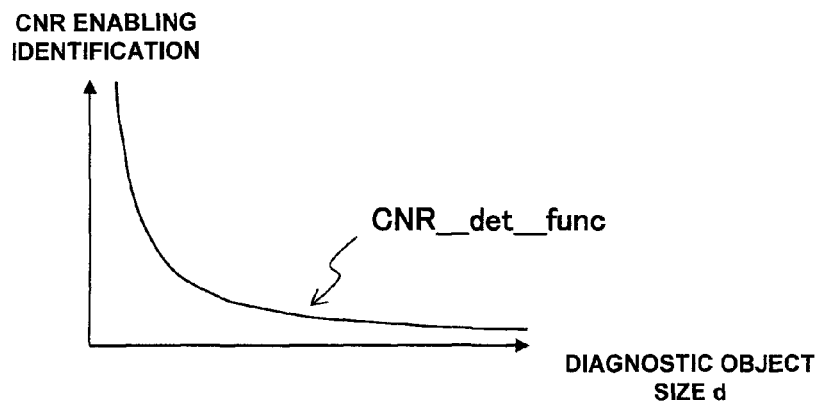
FIG. 6 is a chart showing the function between the diagnostic object size and the CNR enabling identification.
Figure 7:
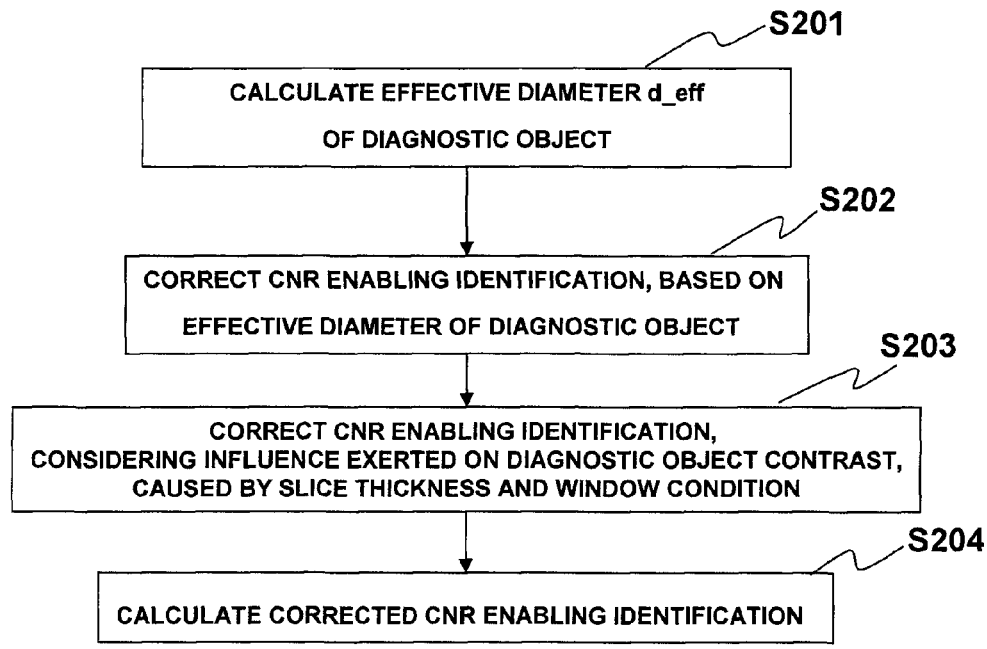
FIG. 7 is a flowchart showing the details of step S200 of the operational flow in FIG. 5.
Figure 11:
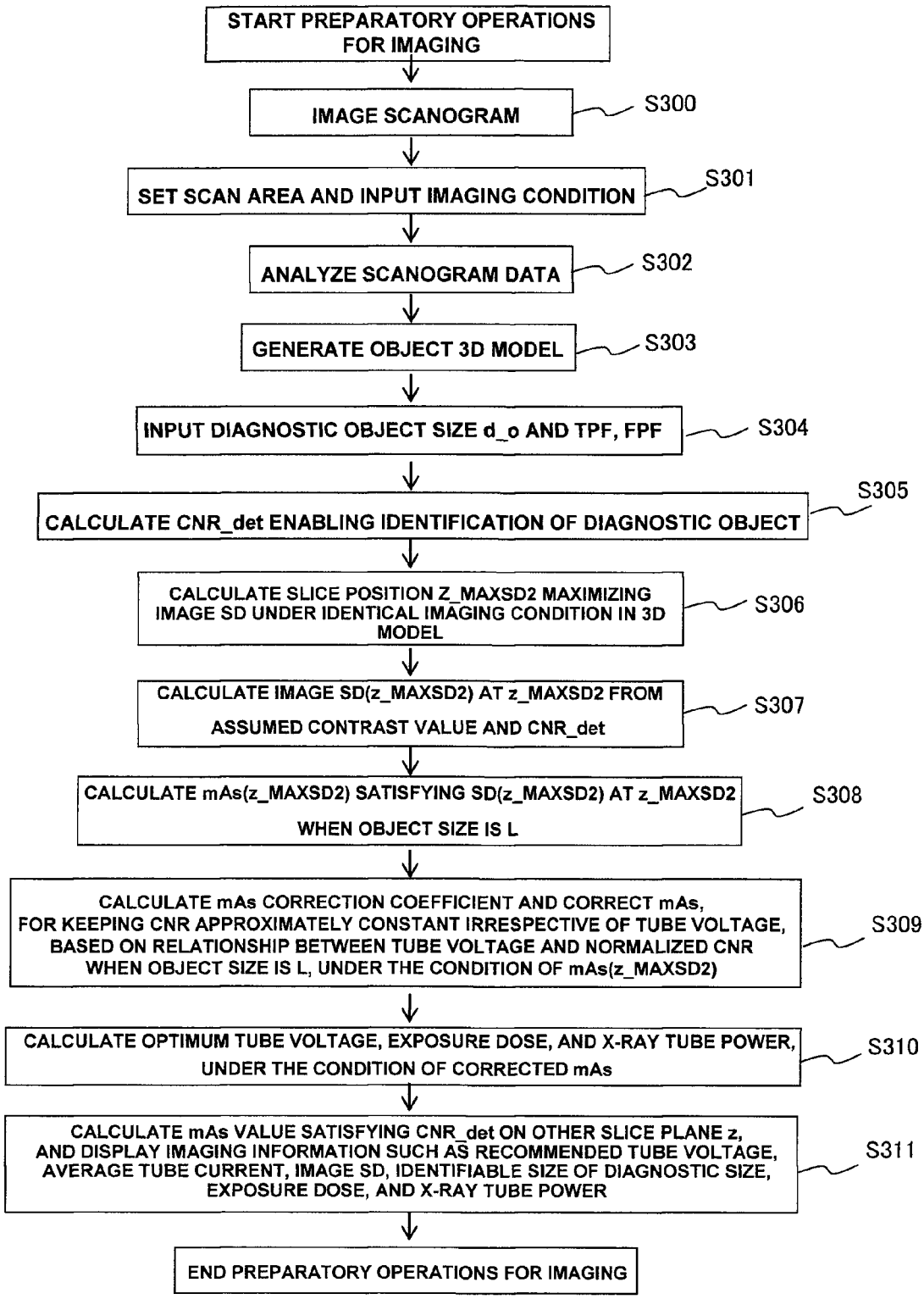
FIG. 11 is an operational flowchart of preparatory operations prior to scanning by the X-ray CT apparatus to which the second embodiment of the present invention is applied.
Figure 12:
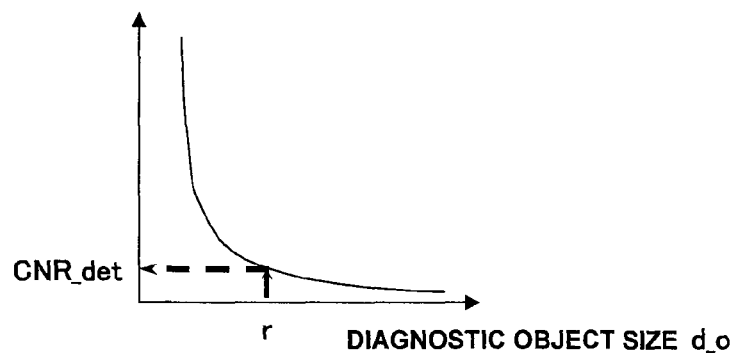
FIG. 12 is a chart showing the relationship between the diagnostic object size and the CNR enabling identification.
Figure 13:
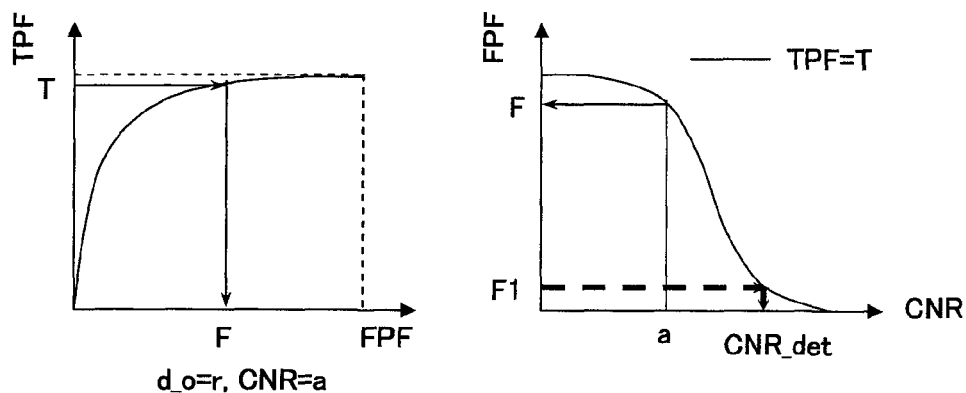
FIG. 13 illustrates the relationship between true positive fraction and the false positive fraction, and the relationship between the CNR enabling identification and the false positive fraction.
Figure 14:
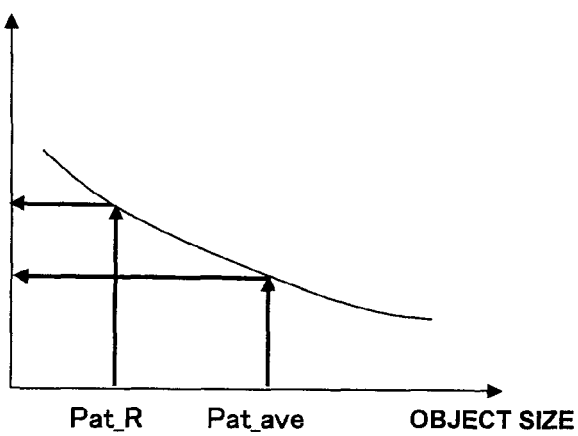
FIG. 14 is a schematic illustration showing the relationship between the average adult object size and the contrast effect normalized by this size, under the condition of standard tube voltage.
Figure 15:
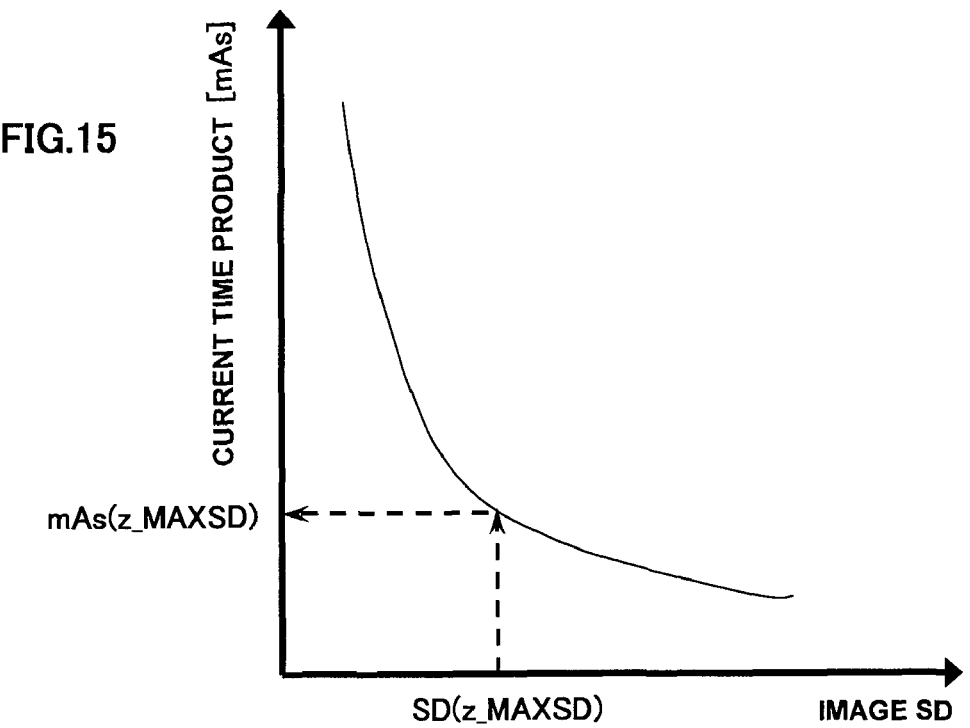
FIG. 15 is a chart showing the relationship between the image SD and tube current time product mAs under the condition of standard tube voltage, with regard to a certain object size.
Figure 16:
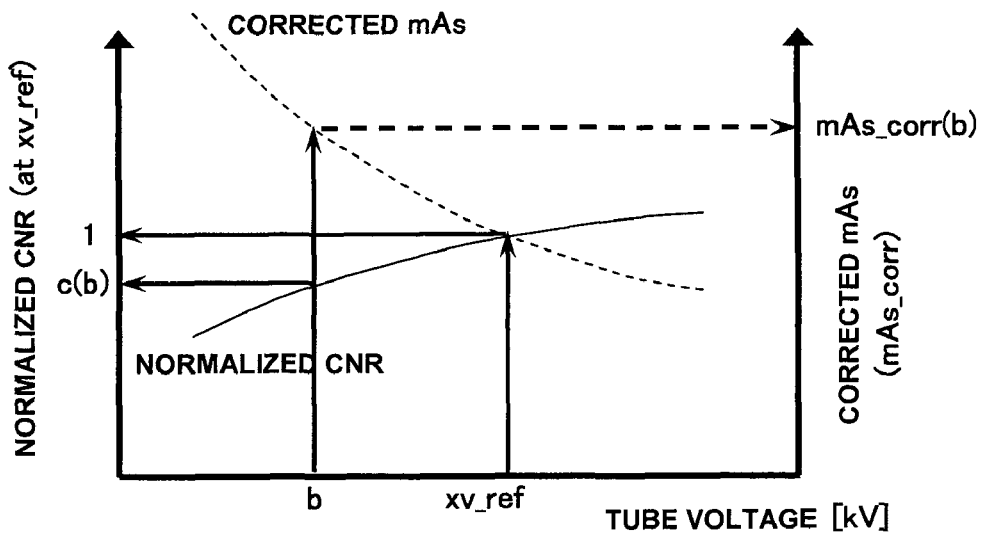
FIG. 16 is a chart showing the relationship among the tube voltage, the normalized CNR, and the corrected tube current time product (corrected mAs), with regard to a certain object size.
Figure 20:
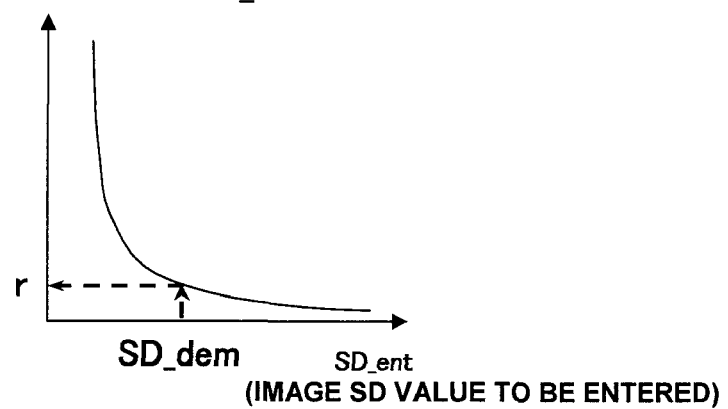
FIG. 20 is a chart showing the relationship between the image SD value to be entered and the diagnostic object size.
Figure 21:
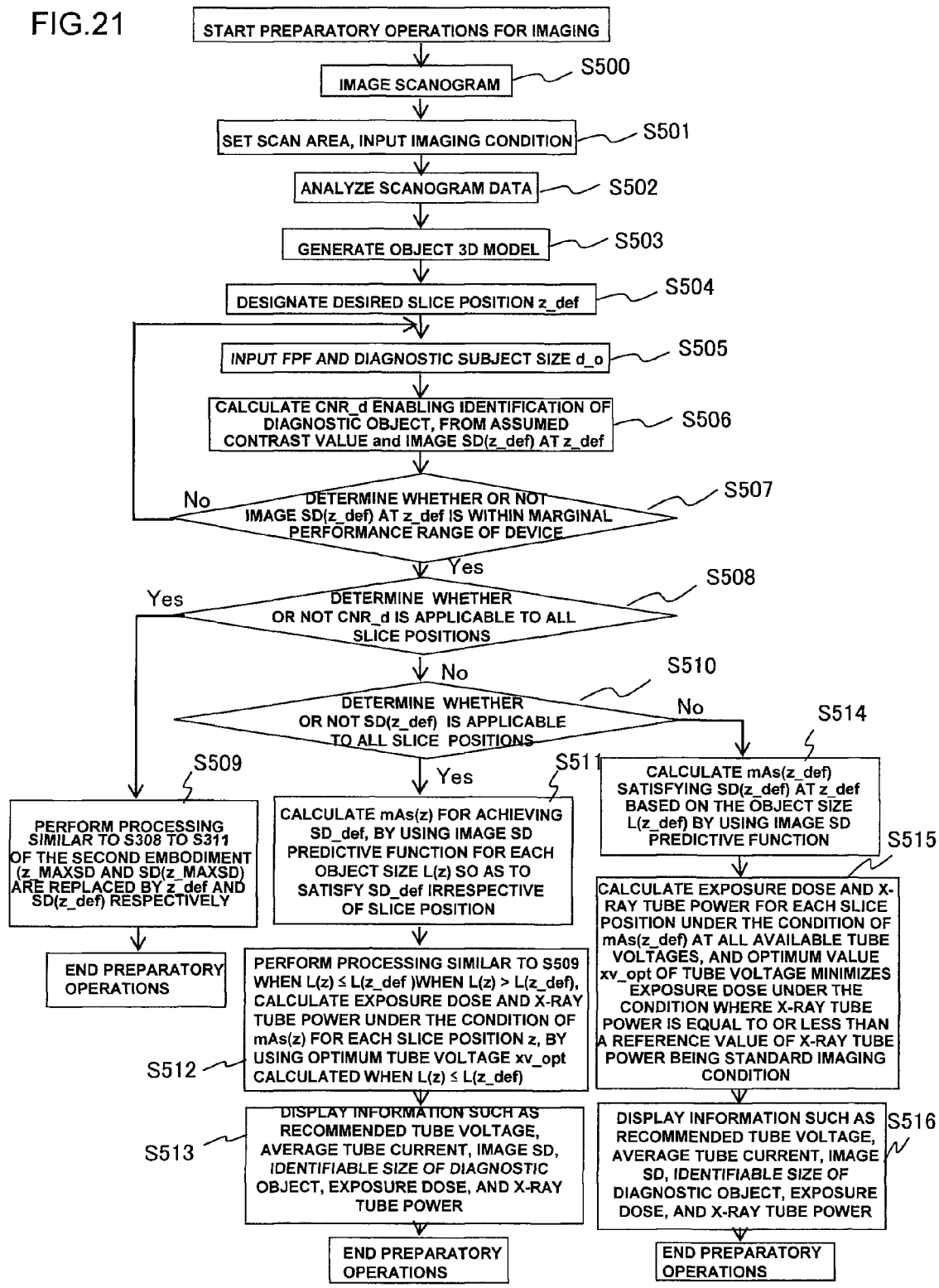
FIG. 21 is an operational flowchart of preparatory operations prior to scanning by the X-ray CT apparatus to which the fourth embodiment of the present invention is applied.
Figure 22:
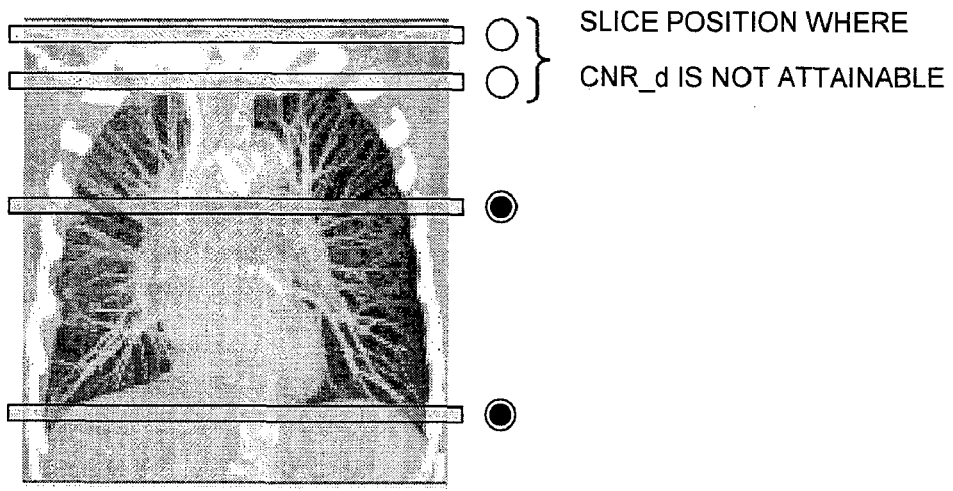
FIG. 22 illustrates a highlighted display of the slice position where the contrast to noise ratio enabling identification cannot be achieved in the diagnostic object area of the designated slice positions.
Figure 24:
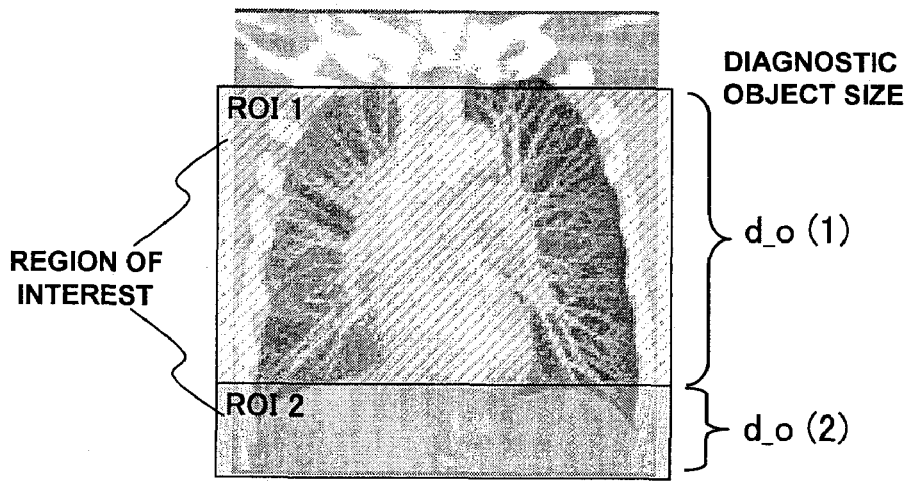
FIG. 24 is a schematic illustration when the number of regions of interest is two.
Figure 23:
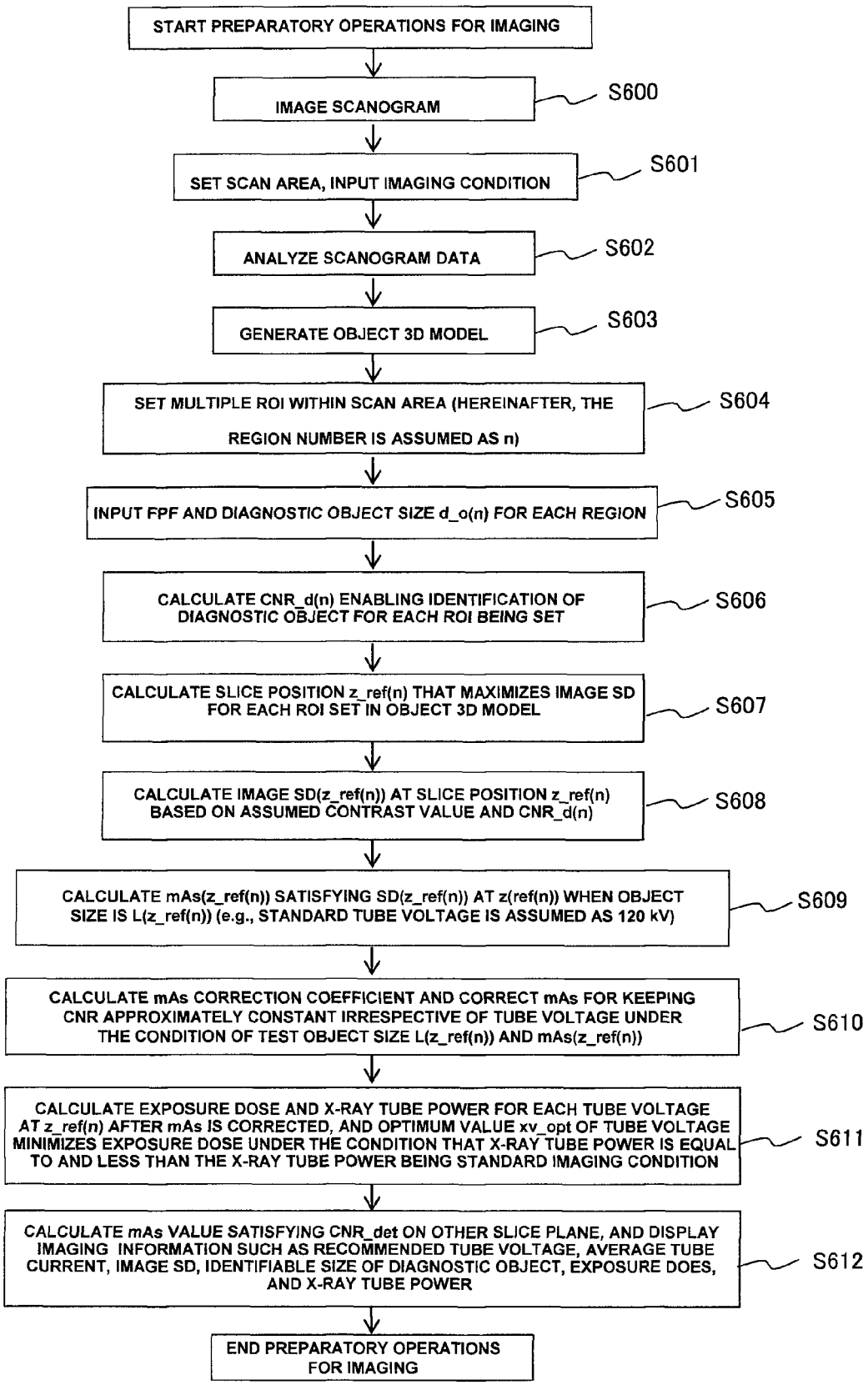
FIG. 23 is an operational flowchart of preparatory operations prior to scanning by the X-ray CT apparatus to which the fifth embodiment of the present invention is applied.
Figure 25:
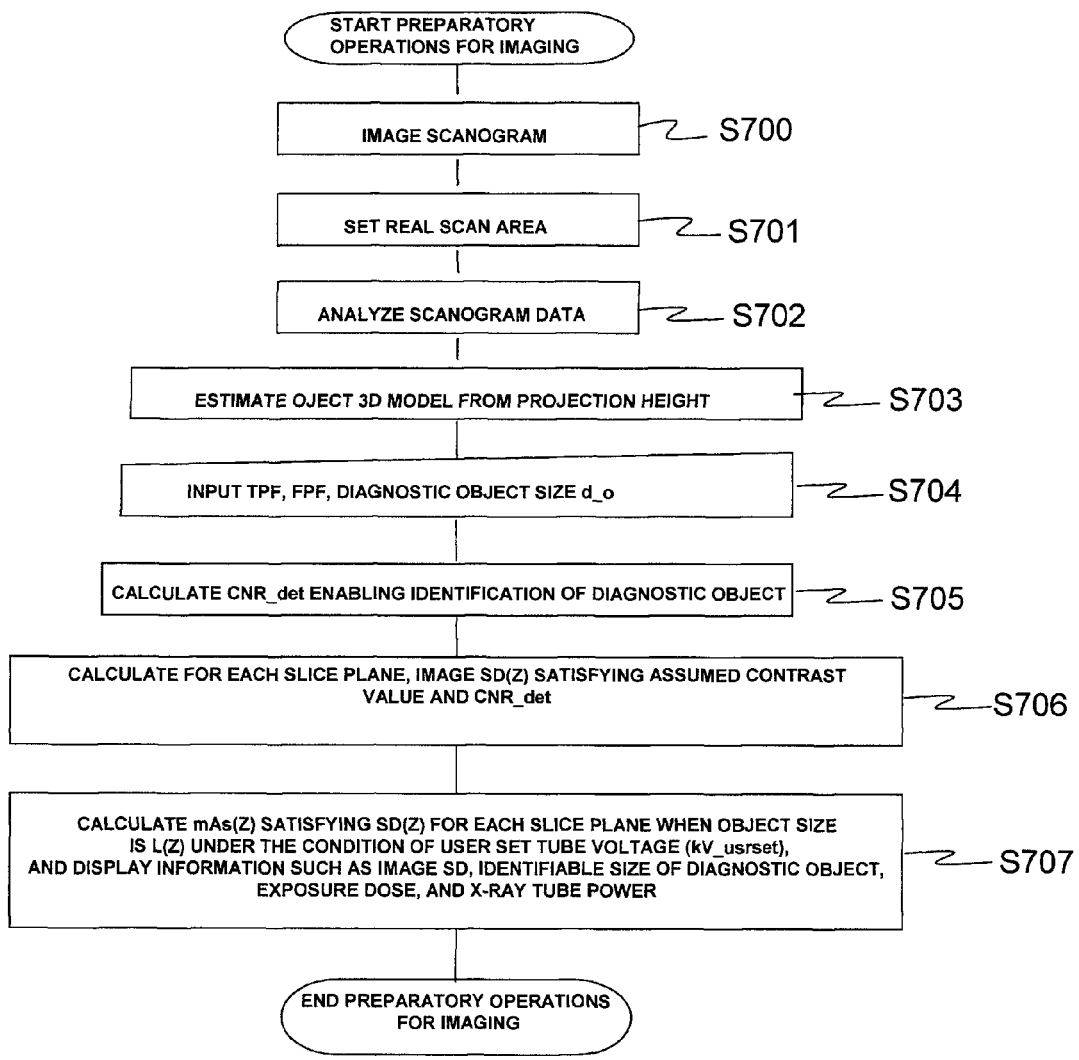
FIG. 25 is an operational flowchart of preparatory operations prior to scanning by the X-ray CT apparatus to which the sixth embodiment of the present invention is applied.
Figure 26:
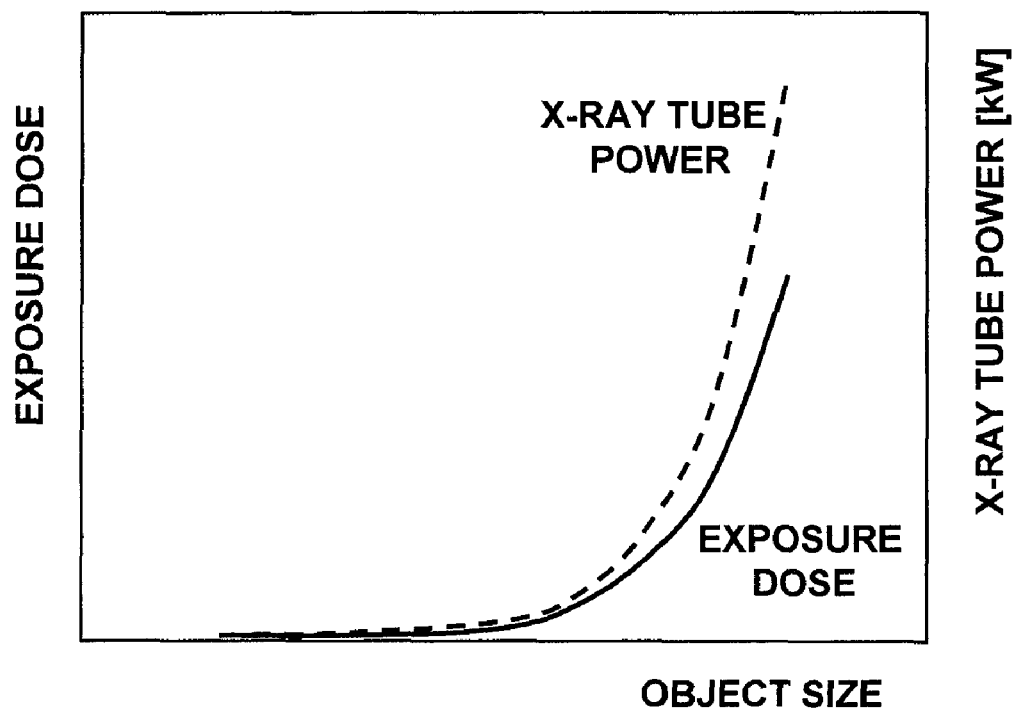
FIG. 26 is a chart showing the relationship between the imaging condition set by the sixth embodiment and the object size.

1 SCANNER GANTRY
2 BED
3 CONSOLE

4 TOP PANEL
5 DISPLAY DEVICE
6 OPERATING DEVICE
7 X-RAY CONTROLLER
8 X-RAY TUBE
9 COLLIMATOR CONTROLLER
10 COLLIMATOR
11 X-RAY DETECTOR
12 DATA COLLECTOR
13 ROTOR PLATE
14 ROTATION CONTROLLER
15 ROTOR PLATE DRIVING DEVICE
16 DRIVE FORCE TRANSMITTER SYSTEM
17 OBJECT
18 X-RAY DETECTOR ELEMENT
19 SYSTEM CONTROLLER
20 BED CONTROLLER
21 BED VERTICAL TRANSFER DEVICE
22 TOP PANEL TRANSFER DEVICE
23 IMAGE RECONSTRUCTION DEVICE
24 STORAGE DEVICE
25 SCAN PLANNING DEVICE
26 OPENING OF SCANNER GANTRY
TPF TRUE POSITIVE FRACTION
FPF FALSE POSITIVE FRACTION
ROI1 ROI2 REGION OF INTEREST

What is claimed is:

1. An X-ray CT apparatus comprising;
an X-ray tube for producing an X-ray to be irradiated to an object,
an X-ray detector being disposed at a position opposed to the X-ray tube so as to place the object between the X-ray tube and the X-ray detector, for detecting the X-ray that has passed through the object,
a scanner rotor being equipped with the X-ray tube and the X-ray detector for rotating around the object,
an operating means for inputting and setting information necessary for a scanogram imaging and a scan imaging, and for carrying out an operation,
an imaging condition decision means for deciding an imaging condition upon scanning, based on scanogram projection data of the object detected by the X-ray detector, and
a scan means for doing a scan under the imaging condition decided by the imaging condition decision means,
the X-ray CT apparatus reconstructing a tomographic image of the object based on a transmitted X-ray dose that is scanned by the scan means and detected by the X-ray detector, wherein,
the imaging condition decision means further comprising,
a storage means for storing a standard imaging condition,
an object three-dimensional model generating means for analyzing the scanogram projection data and generating an object three-dimensional model,
a diagnostic object size setting means for setting a diagnostic object size of the object by the operating means, and
an X-ray condition calculating means for calculating an X-ray condition to obtain a contrast to noise ratio for identifying the diagnostic object, from the diagnostic object size being set, the object three-dimensional model, and the standard imaging condition.

2. The X-ray CT apparatus according to claim 1, wherein,
the X-ray condition calculating means further comprises a contrast to noise ratio calculating means for calculating a contrast to noise ratio to identify the diagnostic object, based on a function stored in the storage means, the function representing a relationship between the diagnostic object size of the object and the contrast to noise ratio for identifying the diagnostic object, and the X-ray condition is calculated by using the contrast to noise ratio obtained from the contrast to noise ratio calculating means.

3. The X-ray CT apparatus according to claim 2, wherein,
the contrast to noise ratio calculating means further comprises a contrast to noise ratio correction means for correcting the contrast to noise ratio calculated based on the function, by using a slice thickness and a window condition inputted via the operating means.

4. The X-ray CT apparatus according to claim 2, wherein,
the X-ray condition calculating means further comprises a true positive false fraction and false positive fraction setting means for setting a true positive false fraction and a false positive fraction in the diagnostic object of the object being set by the diagnostic object size setting means, and
the contrast to noise calculating means generates a function representing the relationship between the diagnostic object size of the object and the contrast to noise ratio for identifying the diagnostic object, based on the true positive fraction, the false positive fraction, and the diagnostic object size being set.

5. The X-ray CT apparatus according to claim 1, wherein, the X-ray condition calculating means comprises,
a first image SD predictive value calculating means for calculating a first image SD predictive value, an image SD value being achieved at each slice position within an imaging region set by the operating means, when using a standard tube voltage and a standard tube current time product constituting the standard imaging condition,
a reference slice position calculating means for calculating a reference slice position that maximizes the first image SD predictive value in a specific slice positional range set within the imaging range,
a contrast to noise ratio calculating means for calculating a contrast to noise ratio for identifying the diagnostic object from the diagnostic object size being set,
a first image SD reference value calculating means for calculating a first image SD reference value at the standard tube voltage, by using the contrast to noise ratio calculated by the contrast to noise ratio calculating means,
a first tube current time product calculating means for calculating a first tube current time product for achieving the first image SD reference value,
a first tube voltage calculating means for calculating a first tube voltage that allows an image SD predictive value to be equal to or less than a predetermined upper limit, when the first tube current time product is used at the reference slice position,
a second image SD reference value calculating means for calculating a second image SD reference value that is achieved by the first tube voltage and the first tube current time product at the reference slice position,
a second image SD predictive value calculating means for calculating a second image SD predictive value that is achieved by the first tube voltage and the first tube current time product at each slice position within the imaging region, and
a second tube current time product calculating means for calculating a second tube current time product for achieving the second image SD reference value at each slice position within the imaging region, from the first tube voltage, the second image SD predictive value, and the second image SD reference value, wherein, the first tube voltage and the second tube current time product are assumed as the X-ray condition.

6. The X-ray CT apparatus according to claim 5, wherein, the contrast to noise ratio calculating means further comprises a means for calculating the contrast to noise ratio, based on a function between the diagnostic object size and a contrast to noise ratio enabling identification.

7. The X-ray CT apparatus according to claim 5, wherein, the first image SD reference value calculating means comprises a means for calculating the first image SD reference value by dividing an assumed contrast value at the standard tube voltage of the diagnostic object, being stored in the storage device, by the contrast to noise ratio calculated by the contrast to noise ratio calculating means.

8. The X-ray CT apparatus according to claim 1, further comprising, a means for displaying expected values of evaluation index, for both of the cases where imaging is performed under the X-ray condition of the first tube voltage and the second tube current time product, and the imaging is performed under another X-ray condition different therefrom, and an X-ray condition selection means for selecting the X-ray condition in association with the expected values of the evaluation index displayed on the display device.

9. The X-ray CT apparatus according to claim 8, wherein, the expected values of the evaluation index include at least one of the tube voltage, a tube current, an exposure dose, the assumed contrast value of the diagnostic object, the contrast to noise ratio, the image SD value, the identifiable size of the diagnostic object, and X-ray tube power consumption.

10. The X-ray CT apparatus according to claim 1, wherein, the X-ray condition calculating means comprises, a true positive fraction and false position fraction setting means for setting a true positive fraction and a false positive fraction in the diagnostic object of the object being set by the diagnostic object size setting means, a contrast to noise ratio calculating means for calculating a contrast to noise ratio for identifying the diagnostic object from the diagnostic object size being set, a slice position calculating means for calculating a reference slice position that maximizes an image SD value under an identical imaging condition in the object three-dimensional model, an image SD value calculating means for calculating an image SD value at the reference slice position, from an assumed contrast value and the contrast to noise ratio calculated by the contrast to noise ratio calculating means, a tube current time product calculating means for calculating a first tube current time product for achieving the image SD value calculated in the image SD value calculating means, a tube current time product correction coefficient calculating means for calculating a tube current time product correction coefficient to keep the contrast to noise ratio approximately constant irrespective of the tube voltage under the condition of the first tube current time product, a tube current time product correction means for correcting the first tube current time product by using the tube current time product correction coefficient, and a tube voltage calculating means for calculating a tube voltage that minimizes an exposure dose, under the condition where power consumed by the X-ray tube is equal to or less than a reference value of X-ray tube power which constitutes the standard imaging condition, wherein, the tube voltage calculated by the tube voltage calculating means and the tube current time product being corrected by the tube current time product correction means are assumed as the X-ray condition.

11. The X-ray CT apparatus according to claim 1, wherein, the X-ray condition calculating means comprises, a slice position calculating means for calculating a reference slice position that maximizes an image SD value under an identical imaging condition in the object three-dimensional model, a target image SD value setting means for inputting and setting a target image SD value from the operating means, a diagnostic object size calculating means for calculating a contrast to noise ratio enabling identification of the diagnostic object of the object from an assumed contrast value at the reference slice position and the target image SD value, so as to calculate a diagnostic object size, a diagnostic object size determination input means for accepting a determination whether or not the diagnostic object size being calculated is appropriate as an actual diagnostic object size, a tube current time product calculating means for calculating a first tube current time product that satisfies the target image SD value in the diagnostic object size at the reference slice position, when it is determined that the diagnostic object size being calculated is appropriate, an image SD value adjusting means for adjusting the target image SD value in such a manner that the diagnostic object size is rendered to be appropriate, when it is determined that the diagnostic object size being calculated is not appropriate, a tube current time product correction coefficient calculating means for calculating a tube current time product correction coefficient that keeps the contrast to noise ratio to be approximately constant irrespective of a tube voltage under the condition of the first tube current time product, a tube current time product correction means for correcting the first tube current time product by the current product correction coefficient, and a tube voltage calculating means for calculating the tube voltage that minimizes an exposure dose, under the condition where power consumed by the X-ray tube is equal to or less than a reference value of X-ray tube power that constitutes the standard imaging condition, wherein, the tube voltage calculated by the tube voltage calculating means and the tube current time product corrected by the tube current time product correction means are assumed as the X-ray condition.

12. The X-ray CT apparatus according to claim 1, wherein, the X-ray condition calculating means comprises;

a desired slice position designating means for designating a desired slice position by the operating means, a false positive fraction setting means for setting a false positive fraction in the diagnostic object of the object being set by the diagnostic object size setting means, a desired slice position image SD value predicting means for calculating an image SD predictive value at the desired slice position from an assumed contrast value and the object three-dimensional model at the desired slice position, a contrast to noise ratio calculating means for calculating a contrast to noise ratio for identifying the diagnostic object at the desired slice position being designated, from the image SD predictive value at the desired slice position and the assumed contrast value, an image SD predictive value feasibility determination means for determining whether or not the image SD predictive value at the desired slice position is feasible, a false positive fraction and diagnostic object size adjusting means for adjusting the false positive fraction and the diagnostic object size so as to achieve a feasible image SD predictive value, when it is determined that the image SD predictive value at the desired slice position is unfeasible, and a contrast to noise ratio determining means for determining whether or not the contrast to noise ratio calculated by the contrast to noise ratio calculating means is applicable to all the slice positions, when it is determined that the image SD predictive value is feasible, wherein, when it is determined that the contrast to noise ratio is applicable to all the slice positions, the X-ray condition calculating means further comprises;

a tube current time product calculating means for calculating a first tube current time product to achieve the image SD predictive value at the desired slice position, a tube current time product correction coefficient calculating means for calculating a tube current time product correction coefficient for keeping the contrast to noise ratio to be approximately constant irrespective of a tube voltage under the condition of the first tube current time product, a tube current time product correction means for correcting the first tube current time product by the tube current time product correction coefficient, and a tube voltage calculating means for calculating the tube voltage that minimizes an exposure dose, under the condition where power consumed by the X-ray tube is equal to or less than a reference value of X-ray tube power that constitutes the standard imaging condition, wherein, the tube voltage calculated by the tube voltage calculating means and the tube current time product corrected by the tube current time product correction means are assumed as the X-ray condition.

13. The X-ray CT apparatus according to claim 12, further comprising, an applicability to all the slice positions determination means for determining whether or not the image SD predictive value at the slice position being designated is applicable to all the slice positions, when the contrast to noise ratio determination means determines that the contrast to noise ratio calculated by the contrast to noise ratio calculating means is not applicable to all the slice positions, a second tube current time product calculating means for calculating a second tube current time product that satisfies, irrespective of the slice position, the image SD predictive value at the desired slice position, when the applicability to all the slice positions determination means determines that the image SD predictive value is applicable to all the slice positions, and an object size comparing means for comparing the object size as to each of the slice positions, and the object size at the desired slice position being designated, wherein, the tube current time product correction coefficient calculating means and the tube current time product correction means calculate a tube current time product correction coefficient to keep the contrast to noise ratio to be approximately constant irrespective of the tube voltage under the condition of the second tube current time product, when it is determined that the object size at the desired slice position being designated is equal to or less than the object size at the scan position in the object size comparing means, and correct the second tube current time product by the correction coefficient, and the tube voltage calculated by the tube voltage calculating means and the tube current time product being corrected by the tube current time product correction means are assumed as the X-ray condition.

14. The X-ray CT apparatus according to claim 13, further comprising;

a third tube current time product calculating means for calculating a third tube current time product that satisfies for each slice position the image SD predictive value at the desired slice position, under the condition of the tube voltage being calculated by the tube voltage calculating means, when the object size comparing means determines that the object size at the slice position is larger than the object size at the slice position being designated, wherein, the tube current time product correction coefficient calculating means and the tube current time product correction means, calculate the tube current time product correction coefficient for keeping the contrast to noise ratio to be approximately constant irrespective of the tube voltage under the condition of the third tube current time product, and correct the third tube current time product by the correction coefficient, and the tube voltage calculated by the tube voltage calculating means and the tube current time product corrected by the tube current time product correction means are assumed as the X-ray condition.

15. The X-ray CT apparatus according to claim 13, further comprising;

a fourth tube current time product calculating means for calculating a fourth tube current time product that satisfies the image SD value at the slice position being designated, when the image SD predictive value at the slice position being designated is not applicable to all the slice positions, an exposure dose and X-ray tube power at the designated slice position calculating means for calculating the exposure dose and the X-ray power at the slice position being designated by using the fourth tube current time product, and a second tube voltage calculating means for calculating a second tube voltage that minimizes the exposure dose under the condition that the X-ray tube power calculated by the calculating means is equal to or less than the reference value of the X-ray tube power which constitutes the standard imaging condition, wherein, the second tube voltage and the fourth tube current time product are assumed as the X-ray condition.

16. The X-ray CT apparatus according to claim 1, wherein, the X-ray condition calculating means comprises, multiple regions of interest (ROI) setting means for setting a scan area by the operating means and for setting multiple regions of interest within the area, a multiple false positive fractions setting means for setting false positive fractions of diseases existing respectively in multiple diagnostic object sizes which are set by the diagnostic object size setting means respectively in the multiple regions of interest set by the multiple ROI setting means, a contrast to noise ratio calculating means for calculating a contrast to noise ratio for identifying the diagnostic object from each of the diagnostic object sizes of the multiple regions of interest being set, a slice position calculating means for calculating a slice position that maximizes an image SD value for each of the regions of interest being set in the object three-dimensional model, an image SD value calculating means for calculating the image SD value at the slice position calculated by the slice position calculating means, from an assumed contrast value and the contrast to noise ratio calculated by the contrast to noise ratio calculating means, a tube current time product calculating means for calculating a tube current time product to achieve the image SD value calculated by the image SD value calculating means, a tube current time product correction coefficient calculating means for calculating a tube current time product correction coefficient for keeping the contrast to noise ratio to be approximately constant irrespective of a tube voltage, under the condition of the tube current time product calculated by the tube current time product calculating means, a tube current time product correction means for correcting the tube current time product calculated by the tube current time product calculating means, by using the tube current time product correction coefficient, and a tube voltage calculating means for calculating the tube voltage that minimizes an exposure dose under the condition where power consumed by the X-ray tube is equal to or less than a reference value of X-ray tube power that constitutes the standard imaging condition, wherein, the tube voltage calculated by the tube voltage calculating means and the tube current time product corrected by the tube current time product correction means are assumed as the X-ray condition.

17. The X-ray CT apparatus according to claim 1, wherein, the X-ray condition calculating means comprises, a true positive fraction and false positive fraction setting means for setting a true positive fraction and a false positive fraction of the diagnostic object of the object set by the diagnostic object size setting means, a contrast to noise ratio calculating means for calculating the contrast to noise ratio for identifying the diagnostic object from the diagnostic object size being set, an image SD value calculating means for calculating an image SD value that satisfies the contrast to noise ratio calculated from an assumed contrast value and the contrast to noise calculating means, for each slice plane existing within a specific slice positional range, and a tube current time product calculating means for calculating a tube current time product that satisfies the image SD value in the diagnostic object size for each slice plane, at the tube voltage set as the standard imaging condition, wherein, the tube voltage being set and the tube current time product being calculated by the tube current time product calculating means are assumed as the X-ray condition.

18. The X-ray CT apparatus according to claim 10, further comprising, a means for displaying expected values of evaluation index when imaging is performed, under the X-ray condition calculated by the X-ray condition calculating means, including the tube voltage and an average tube current obtained by dividing the tube current time product by a scan time, and under another X-ray condition different therefrom.

19. The X-ray CT apparatus according to claim 18, wherein, the expected values of the evaluation index include at least one of a recommended tube voltage being the tube voltage, the average tube current, the false positive fraction, an identifiable size of the diagnostic object, the image SD value, the exposure dose, and the X-ray tube power consumption.

20. The X-ray CT apparatus according to claim 18, further comprising, an X-ray condition selection means for selecting the X-ray condition in association with the expected values of the evaluation index being displayed on the display device.

\* \* \* \* \*